(12) United States Patent
Hoppin et al.

(10) Patent No.: US 10,209,242 B2
(45) Date of Patent: Feb. 19, 2019

(54) FLUORESCENCE HISTO-TOMOGRAPHY (FHT) SYSTEMS AND METHODS

(71) Applicants: inviCRO, LLC, Boston, MA (US); Curadel, LLC, Marlborough, MA (US)

(72) Inventors: John W. Hoppin, Boston, MA (US); John V. Frangioni, Worcester, MA (US); Robert William Holt, Boston, MA (US); Mohammed Q. Qutaish, Medford, MA (US); Marc Edward Seaman, Norwood, MA (US); Mark W. Bordo, Worcester, MA (US); Jacob Yost Hesterman, Newton, MA (US)

(73) Assignee: EMIT IMAGING, INC., Boston, MA (US)

( * ) Notice: Subject to any disclaimer, the term of this patent is extended or adjusted under 35 U.S.C. 154(b) by 146 days.

(21) Appl. No.: 15/253,149

(22) Filed: Aug. 31, 2016

(65) Prior Publication Data

US 2016/0370349 A1 Dec. 22, 2016

Related U.S. Application Data

(63) Continuation-in-part of application No. 15/158,928, filed on May 19, 2016, now Pat. No. 9,799,113.
(Continued)

(51) Int. Cl.
*G06T 7/30* (2017.01)
*A61B 5/00* (2006.01)
(Continued)

(52) U.S. Cl.
CPC ....... *G01N 33/5023* (2013.01); *A61B 5/0073* (2013.01); *G06T 5/003* (2013.01);
(Continued)

(58) Field of Classification Search
CPC ....... G01N 33/5023; G06T 7/30; G06T 5/003; A61B 5/0073; A61B 5/0071; H04N 5/247; H04N 5/2252
See application file for complete search history.

(56) References Cited

U.S. PATENT DOCUMENTS 5,136,906 A * 8/1992 Antonissen ........ A22C 17/0033
382/110
6,330,348 B1 12/2001 Kerschmann et al.
(Continued)

FOREIGN PATENT DOCUMENTS

CN 101008590 A 8/2007
DE 102005042367 A1 3/2007
(Continued)

OTHER PUBLICATIONS

Shen et al., "Automated Fluorescence and Reflectance Coregistered 3-D Tissue Imaging System," IEEE Transactions on Magnetics, vol. 49, No. 1, Jan. 2013, pp. 279-283.
(Continued)

*Primary Examiner* — Jon Chang
(74) *Attorney, Agent, or Firm* — Parker Ibrahim & Berg LLP; Stephen D. LeBarron

(57) ABSTRACT

In one embodiment, a fluorescence histo-tomography (FHT) system is disclosed. The FHT system includes a housing, a fluorescence camera located within the housing, a white light camera located within the housing, and a fluorescence light source located within the housing. The FHT system further includes a support mount configured to support the housing within a chamber of a slicing apparatus such that the cameras and fluorescence light source are aimed towards a block face of a tissue specimen retained within the chamber.

18 Claims, 26 Drawing Sheets
(11 of 26 Drawing Sheet(s) Filed in Color)

Related U.S. Application Data

(60) Provisional application No. 62/211,930, filed on Aug. 31, 2015, provisional application No. 62/164,800, filed on May 21, 2015.

(51) Int. Cl.
  *G06T 5/00* (2006.01)
  *G01N 33/50* (2006.01)
  *H04N 5/225* (2006.01)
  *H04N 5/247* (2006.01)

(52) U.S. Cl.
  CPC ............. *G06T 7/30* (2017.01); *H04N 5/2252* (2013.01); *H04N 5/247* (2013.01); *A61B 5/0071* (2013.01)

(56) References Cited

U.S. PATENT DOCUMENTS

| | | |
|---|---|---|
| 6,387,653 B1 | 5/2002 | Voneiff et al. |
| 7,582,872 B2 | 9/2009 | Lewis et al. |
| 7,600,457 B2 | 10/2009 | Voneiff et al. |
| 7,677,289 B2 | 3/2010 | Hayworth et al. |
| 7,767,414 B1 | 8/2010 | Smith et al. |
| 7,831,075 B2 | 11/2010 | Wilson et al. |
| 8,074,547 B2 | 12/2011 | Ito et al. |
| 8,238,632 B2 | 8/2012 | Wilson et al. |
| 8,366,857 B2 | 2/2013 | Hayworth et al. |
| 8,386,015 B2 | 2/2013 | Kamen et al. |
| 8,640,585 B2 | 2/2014 | Zust et al. |
| 8,687,858 B2 | 4/2014 | Walter et al. |
| 8,744,163 B2 | 6/2014 | Morris |
| 8,771,978 B2 | 7/2014 | Ragan |
| 8,787,651 B2 | 7/2014 | Potts et al. |
| 8,839,700 B2 | 9/2014 | Chen et al. |
| 8,995,733 B2 | 3/2015 | Van Dijk et al. |
| 9,008,378 B2 | 4/2015 | Micheva et al. |
| 9,109,982 B2 | 8/2015 | Nakajima et al. |
| 9,117,102 B2 | 8/2015 | Thomas et al. |
| 2005/0253087 A1 | 11/2005 | Plan |
| 2007/0083124 A1 | 4/2007 | Ehben et al. |
| 2009/0236541 A1 | 9/2009 | Lomnes et al. |
| 2010/0000383 A1* | 1/2010 | Koos ............... G01N 1/06 83/22 |
| 2011/0091088 A1 | 4/2011 | Wilson et al. |
| 2011/0152714 A1 | 6/2011 | Luginbuhl et al. |
| 2014/0030757 A1 | 1/2014 | Schiffenbauer |
| 2014/0248210 A1 | 9/2014 | Bradbury et al. |
| 2015/0017679 A1 | 1/2015 | Ito |

FOREIGN PATENT DOCUMENTS

| | | |
|---|---|---|
| DE | 60033923 T2 | 11/2007 |
| DE | 102009022157 A1 | 2/2010 |
| DE | 102009061014 B4 | 3/2012 |
| DE | 202013103215 U1 | 8/2013 |
| EP | 1826547 A2 | 8/2007 |
| GB | 2462360 A | 2/2010 |
| JP | 2007-198832 | 8/2007 |
| JP | 5103447 B2 | 12/2012 |

OTHER PUBLICATIONS

Delaquis et al., "Development of a camera casing suited for cryogenic and vacuum applications," ArXiv, Oct. 24, 2013, pp. 1-11.
International Search Report and Written Opinion dated Nov. 17, 2016 issued in connection with PCT/US16/49708.
Bernard et al. "High spatial resolution measurements of organ blood flow in small laboratory animals" Am J Physiol Heart Circ Physiol 279: H2043-H2052, May 18, 2000; pp. 1-10.

* cited by examiner

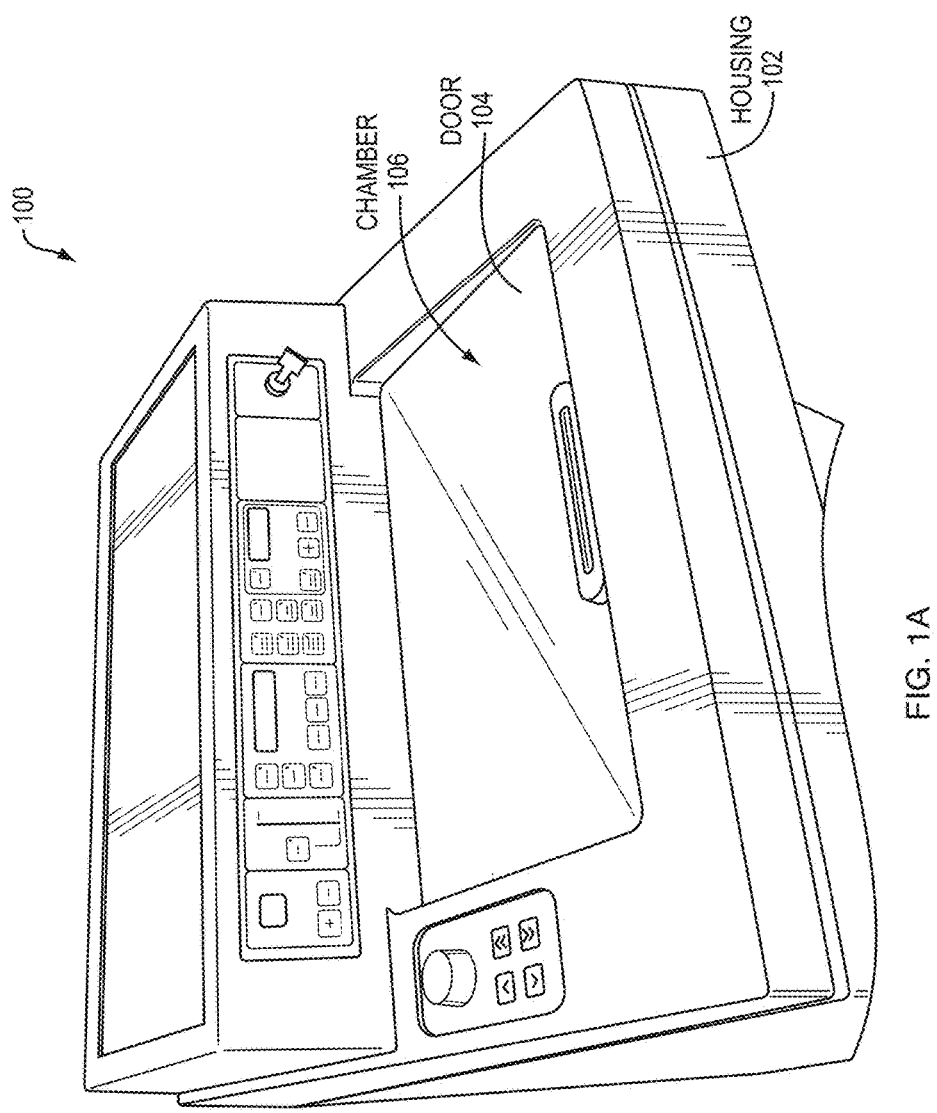

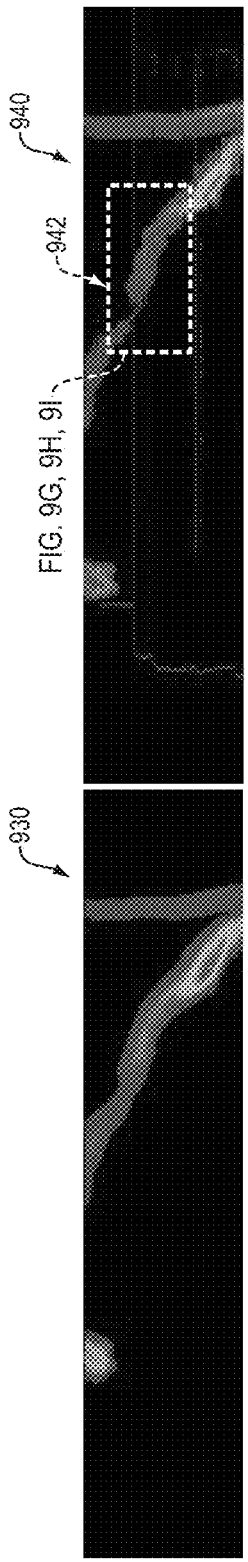
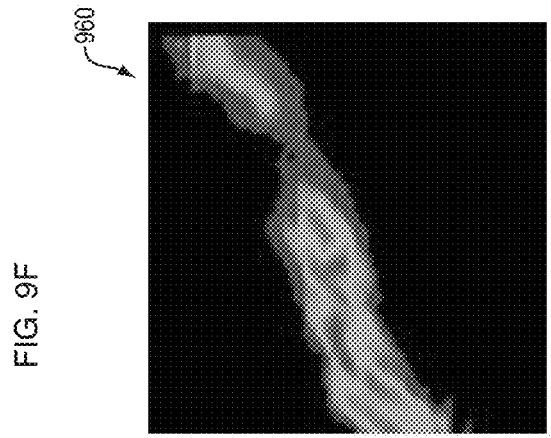
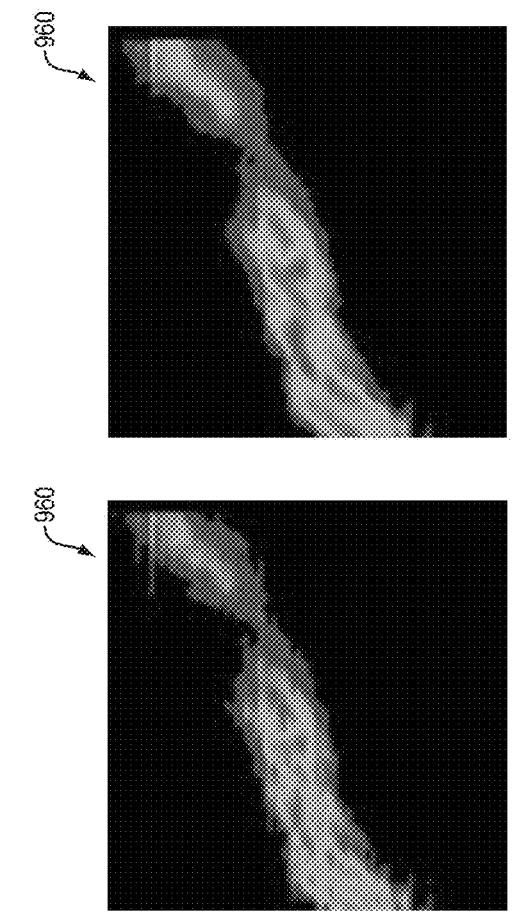
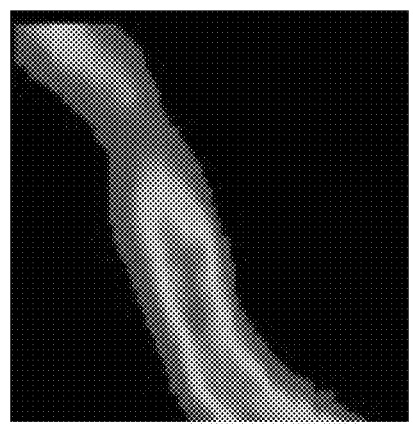
FIG. 9E ORIGINAL
FIG. 9F AFTER SUBTRACTION-BASED DEBLURRING
FIG. 9G ORIGINAL
FIG. 9H AFTER SUBTRACTION-BASED DEBLURRING
FIG. 9I WITH EDGE-PRESERVING SMOOTHING

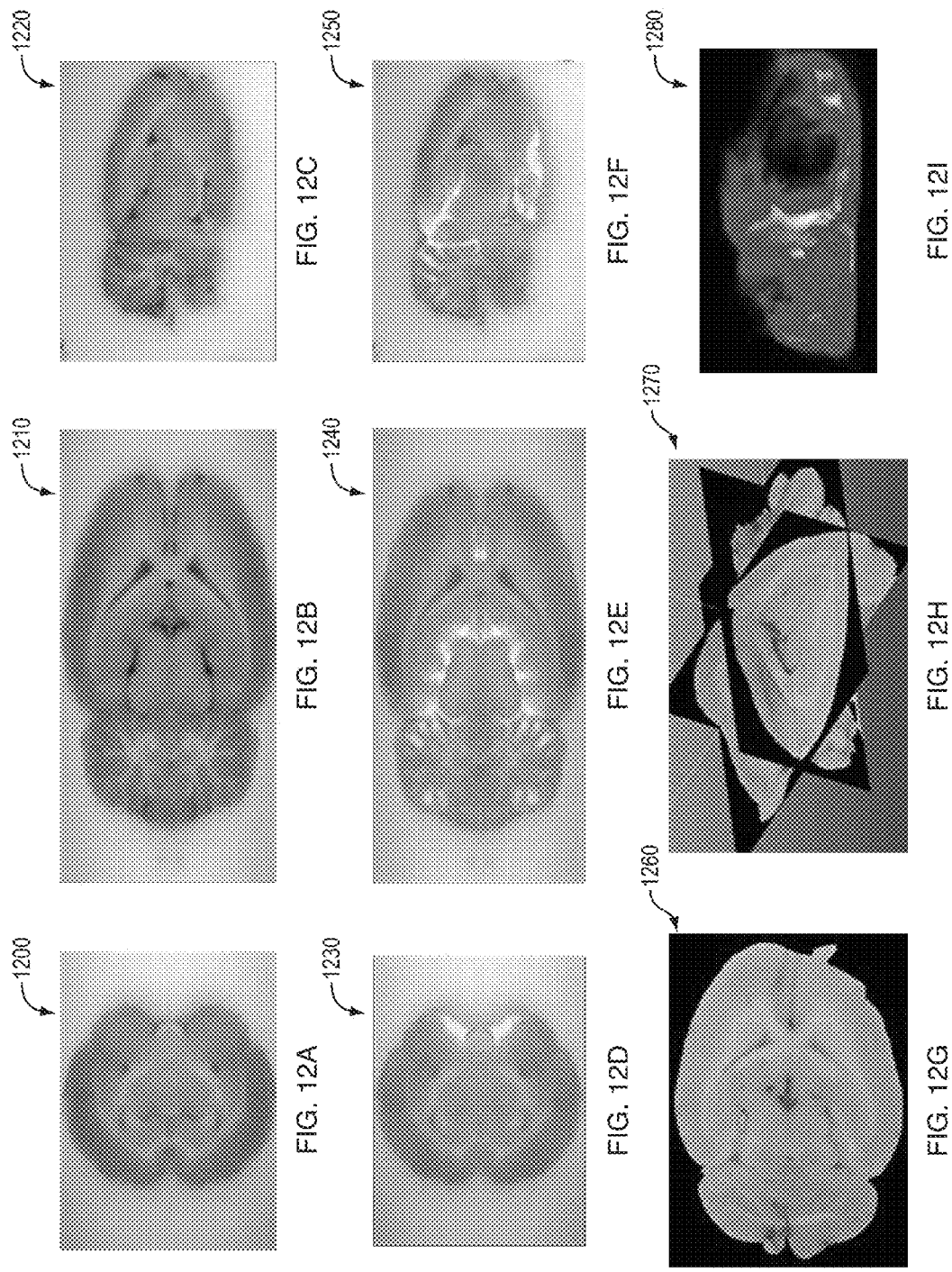

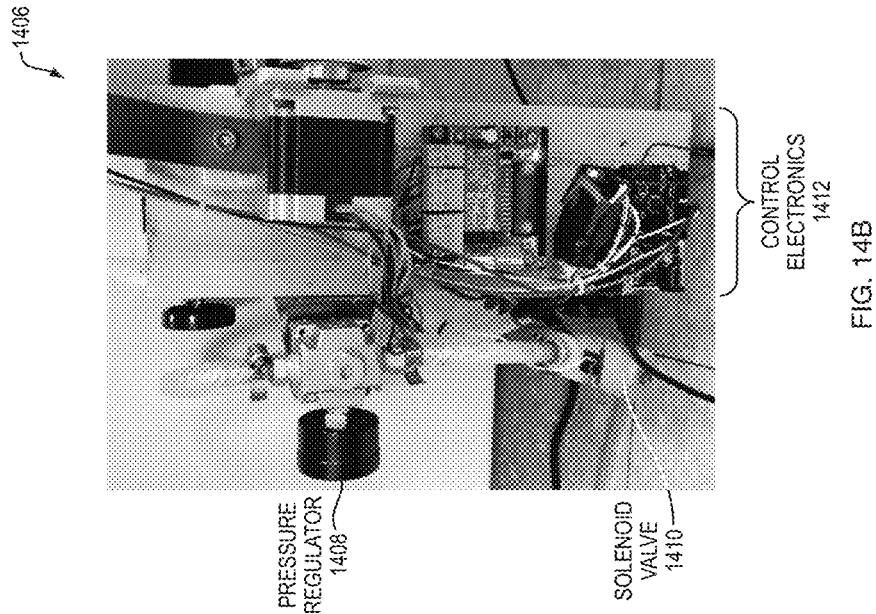

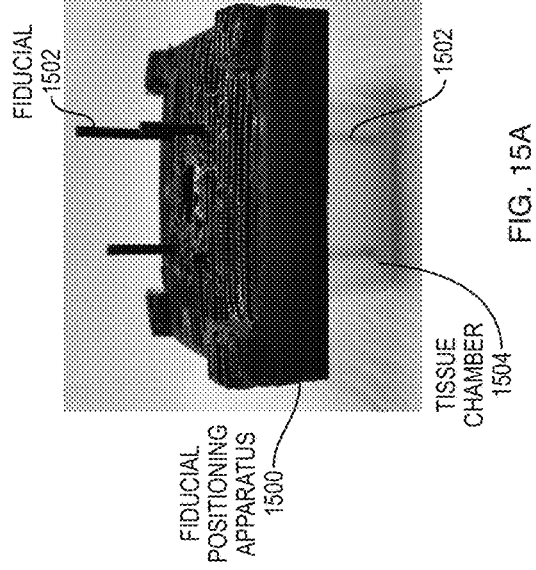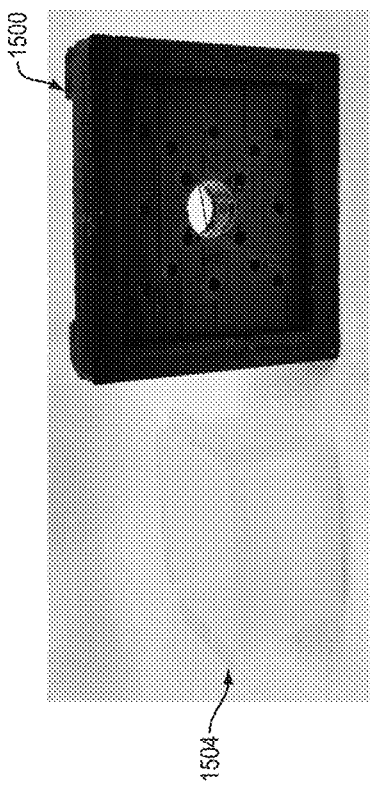
FIG. 15A
FIG. 15B

FLUORESCENCE HISTO-TOMOGRAPHY (FHT) SYSTEMS AND METHODS

RELATED APPLICATIONS

This application claims priority to U.S. Provisional Application No. 62/211,930, filed on Aug. 31, 2015, entitled "CRYOFLUORESCENCE TOMOGRAPHY (FHT) SYSTEMS AND METHODS," by Hoppin, et al., and to U.S. Non-Provisional application Ser. No. 15/158,928, filed on May 19, 2016, entitled "MULTI-SPECTRAL THREE DIMENSIONAL IMAGING SYSTEM AND METHOD," which claims priority to U.S. Provisional Application No. 62/164,800, filed on May 21, 2015, entitled "MULTI-SPECTRAL THREE DIMENSIONAL IMAGING SYSTEM AND METHOD," the contents all of which are herein incorporated by reference.

TECHNICAL FIELD

The present disclosure relates generally to imaging and, more specifically, to fluorescence histo-tomography (FHT) systems and methods.

BACKGROUND

Multispectral fluorescence tissue slice imaging can be used to measure drug distribution ex-vivo in standalone or retrofitted slice imagers. Such specificity in a single imaging system can result in a high cost per scan. For high throughput and low cost, it would be valuable to construct a fluorescence histological (histo-) imager with a corresponding software package that can work in tandem with slicing instruments. To that end, the methods outlined here demonstrate a workflow of fluorescence imaging techniques for a versatile, transportable add-on to existing histological slicing instruments.

SUMMARY

According to one or more embodiments of the disclosure as described in greater detail below, a fluorescence histo-tomography (FHT) system is disclosed. The FHT system includes a housing, a fluorescence camera located within the housing, a white light camera located within the housing, and a fluorescence light source located within the housing. The FHT system further includes a support mount configured to support the housing within a chamber of a slicing apparatus such that the cameras and fluorescence light source are aimed towards a block face of a tissue specimen retained within the chamber.

In further embodiments, a method for performing FHT is disclosed. The method includes capturing, by an imaging device mounted within a chamber of a slicing apparatus, a white light image of a block face of a tissue specimen retained within the chamber. The method also includes capturing, by the imaging device, a fluorescence image of the block face under white light and fluorescence illumination. The method further includes co-registering, by the imaging device, the white light and fluorescence images to form a combined image. The method additionally includes providing, by the imaging device, the combined image to an electronic display.

In additional embodiments, a FHT system is disclosed. The FHT system includes means for imaging a block face of a tissue specimen retained within a chamber of a slicing apparatus. The FHT system also includes means for supporting the imaging means within the chamber of the slicing apparatus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects, features, aspects and advantages of the embodiments disclosed herein will become more apparent from the following detailed description when taken in conjunction with the following accompanying drawings.

FIGS. 1A-1B illustrate an example cryostat/cryomicrotome, according to various embodiments.

FIGS. 9A-9I illustrate test results of FHT imaging of a fluorophore-infused piece of twine, according to various embodiments.

FIGS. 12A-12I illustrate additional examples of FHT imaging of brain tissue, according to various embodiments.

FIGS. 14A-14C illustrate examples of a mechanism to remove stuck tissues slices from an FHT system.

FIGS. 15A-15B illustrate an example apparatus for precisely placing fiducial markers in a tissue block.

Figure 1B:
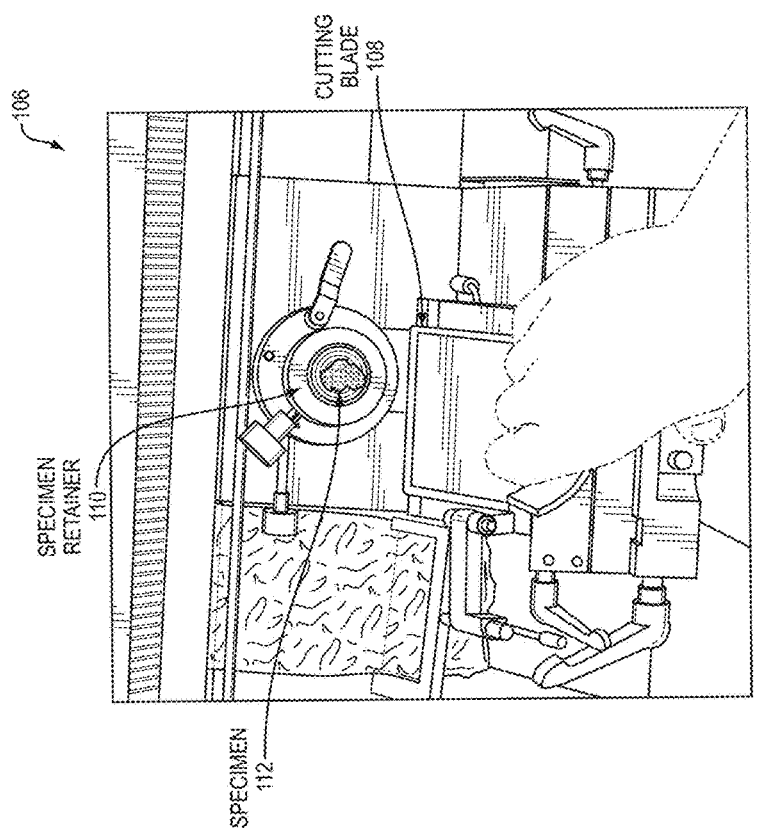

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Various challenges persist to find otherwise invisible, small objects in a body. Labeling such objects with fluorophores is a possible technique to introduce contrast, but visible fluorophores are problematic because excitation light and emission light are both absorbed and scattered. Nearinfrared (NIR) fluorescent light has the ability to provide high contrast in the context of normal bodily tissues and fluids.

Histological analysis of sections from previously living tissue is time-consuming and laborious because each section needs to be mounted, processed, and scanned (e.g., using a microscope). Block face imaging is the opposite of conventional analysis because the tissue slice is thrown away and only the exposed block face of the tissue specimen is imaged. When using NIR fluorescent light to image the block face, extremely high signal to noise is achieved, although one also has to attempt to compensate for the "extra depth" that NIR can see. In some implementations, video information (e.g., color, grayscale, etc.) as well as assumptions about light propagation in the tissue can be used to generate at least an approximation of the actual fluorescence.

In some aspects, the techniques described herein utilize simultaneous color/NIR acquisition to acquire data sets and mathematical methods applied to these data sets to reconstruct in ultra-high resolution, at least an approximation of the actual NIR fluorescence present in the tissue block and therefore the original living tissue. NIR also provides high sensitivity and less interference from endogenous chromophores that would otherwise preclude visible fluorescence imaging.

Referring now to FIG. 1A, a cryostat/cryomicrotome 100 is shown, according to various embodiments. In general, a microtome is a device typically used to prepare histologic samples of a tissue block for use in microscopy. For example, a microtome may shave a thin layer of a tissue specimen from a tissue block that can then be mounted to a slide for observation using a microscope. A cryomicrotome is a specialized form of microtome operable to keep the tissue specimen at a reduced temperature during slicing. While the FHT system disclosed herein is described with respect to a cryomicrotome, the teachings herein are not limited as such. In particular, the FHT system can be implemented using any number of different slicing devices (e.g., other microtomes, histological sample preparation devices, macrotomes, etc.).

As shown, cryomicrotome 100 may include a housing 102 that encompasses a sealed chamber 106 in which the cutting operation is performed. Cryomicrotome 100 may also include a door 104 or other access mechanism (e.g., lid, etc.) that afford the user of cryomicrotome 100 access to chamber 106. During use, cryomicrotome 100 may regulate the internal temperature of chamber 106 to prevent a frozen tissue specimen being sliced from thawing back to room temperature.

FIG. 1B illustrates an example chamber 106 of cryomicrotome 100 in greater detail. As shown, cryomicrotome 100 may include a specimen retainer 110 that holds a frozen specimen 112 in place. In addition, cryomicrotome 100 may also include one or more cutting blades 108 that, when actuated, moves across the block face of specimen 112 to remove a thin layer of specimen 112. In many cases, specimen 112 may be any form of biological material extricated from a subject and may be frozen in an optimal cutting temperature (OCT) material, prior to placement in cryomicrotome 100.

The alignment of cutting blade 108 and specimen retainer 110 may be configurable in some cryomicrotomes to adjust, e.g., the thickness of the resulting tissue slice and/or to ensure proper contact of cutting blade 108 with tissue specimen 112. For example, a user of cryomicrotome 100 may first ensure the correct positions of tissue specimen 112 before initiating slicing of the tissue specimen 112. In some embodiments, actuation of cutting blade 108 may be performed manually by the user. In other embodiments, actuation of cutting blade 108 and/or movement of specimen retainer 110 may be performed automatically by cryomicrotome 100 under computerized control.

An exemplary cryomicrotome that can be used to implement the techniques herein is the Leica 3050 cryomicrotome available from Leica Camera AG, Wetzlar, Germany. However, as would be appreciated, the techniques herein can be applied to any number of different cryomicrotomes and are not limited to a particular make, model, or type of cryomicrotome.

As noted above, NIR fluorescence imaging has emerged in recent years and demonstrates the ability to produce images with high contrast between fluorophore infused tissue and regular tissue. Table 1 below provides a listing of exemplary fluorophore agents with their peak excitation wavelengths (Ex) and peak emission wavelengths (Em).

TABLE 1

| Type | Agent | Ex (nm) | Em (nm) |
|---|---|---|---|
| Reactive and conjugated probes | Hydroxycoumarin | 325 | 386 |
| | Aminocoumarin | 350 | 455 |
| | Methoxycoumarin | 360 | 410 |
| | Cascade Blue | 375; 400 | 423 |
| | Lucifer Yellow | 425 | 528 |
| | NBD | 466 | 539 |
| | R-Phycoerythrin (PE) | 480; 565 | 578 |
| | PE-Cy5 conjugates | 480; 565; 650 | 670 |
| | PE-Cy7 conjugates | 480; 565; 743 | 767 |
| | APC-Cy7 conjugates | 650; 755 | 767 |
| | Red 613 | 480; 565 | 613 |
| | Fluorescein | 495 | 519 |
| | FluorX | 494 | 520 |
| | BODIPY-FL | 503 | 512 |
| | TRITC | 547 | 574 |
| | X-Rhodamine | 570 | 576 |
| | Lissamine Rhodamine B | 570 | 590 |
| | PerCP | 490 | 675 |
| | Texas Red | 589 | 615 |
| | Allophycocyanin (APC) | 650 | 660 |
| | TruRed | 490, 675 | 695 |
| | Alexa Fluor 350 | 346 | 445 |
| | Alexa Fluor 430 | 430 | 545 |
| | Alexa Fluor 488 | 494 | 517 |
| | Alexa Fluor 532 | 530 | 555 |
| | Alexa Fluor 546 | 556 | 573 |
| | Alexa Fluor 555 | 556 | 573 |
| | Alexa Fluor 568 | 578 | 603 |
| | Alexa Fluor 594 | 590 | 617 |
| | Alexa Fluor 633 | 621 | 639 |
| | Alexa Fluor 647 | 650 | 688 |
| | Alexa Fluor 660 | 663 | 690 |
| | Alexa Fluor 680 | 679 | 702 |
| | Alexa Fluor 700 | 696 | 719 |
| | Alexa Fluor 750 | 752 | 779 |
| | Cy2 | 489 | 506 |
| | Cy3 | (512); 550 | 570; (615) |
| | Cy3, 5 | 581 | 596; (640) |
| | Cy5 | (625); 650 | 670 |
| | Cy5, 5 | 675 | 694 |
| | Cy7 | 743 | 767 |
| | ZW800-1 | 760 | 790 |
| | ZW700-1 Forte | 675 | 700 |
| | Lipo800-Forte | 760 | 790 |
| | Lipo700-Forte | 675 | 700 |
| Nucleic acid probes | Hoechst 33342 | 343 | 483 |
| | DAPI | 345 | 455 |
| | Hoechst 33258 | 345 | 478 |
| | SYTOX Blue | 431 | 480 |
| | Chromomycin A3 | 445 | 575 |
| | Mithramycin | 445 | 575 |
| | YOYO-1 | 491 | 509 |
| | SYTOX Green | 504 | 523 |
| | SYTOX Orange | 547 | 570 |

TABLE 1-continued

| Type | Agent | Ex (nm) | Em (nm) |
|---|---|---|---|
| | Ethidium Bormide | 493 | 620 |
| | 7-AAD | 546 | 647 |
| | Acridine Orange | 503 | 530/640 |
| | TOTO-1, TO-PRO-1 | 509 | 533 |
| | Thiazole Orange | 510 | 530 |
| | Propidium Iodide (PI) | 536 | 617 |
| | TOTO-3, TO-PRO-3 | 642 | 661 |
| | LDS 751 | 543; 590 | 712; 607 |
| Fluorescent | Y66F | 360 | 508 |
| Proteins | Y66H | 360 | 442 |
| | EBFP | 380 | 440 |
| | Wild-type | 396, 475 | 50, 503 |
| | GFPuv | 385 | 508 |
| | ECFP | 434 | 477 |
| | Y66W | 436 | 485 |
| | S65A | 471 | 504 |
| | S65C | 479 | 507 |
| | S65L | 484 | 510 |
| | S65T | 488 | 511 |
| | EGFP | 489 | 508 |
| | EYFP | 514 | 527 |
| | DsRed | 558 | 583 |
| Other probes | Monochlorobimane | 380 | 461 |
| | Calcein | 496 | 517 |

In many cases, the fluorophores that can be used for purposes of fluorescence imaging may exhibit emission spectra in the range of approximately 200 nm to 1000 nm. Further, a plurality of fluorophores can be used on a single specimen if each of the used fluorophores has different emission spectra. Other fluorophores not listed in Table 1 can also be used without deviating from the teachings herein.

According to various embodiments, NIR fluorescence imaging can be leveraged with a cryomicrotome to perform fluorescence histo-tomography (FHT) of a tissue specimen. As noted, cryomicrotomes are typically used to prepare tissue slices for further analysis (e.g., by mounting a slice to a microscope slide, etc.). In contrast, the FHT techniques herein propose the exact opposite, i.e., by imaging the exposed block face of the tissue specimen itself while in the cryomicrotome without any regard to the resultant tissue slices, which may be discarded or retained as desired by the user.

Figure 2:
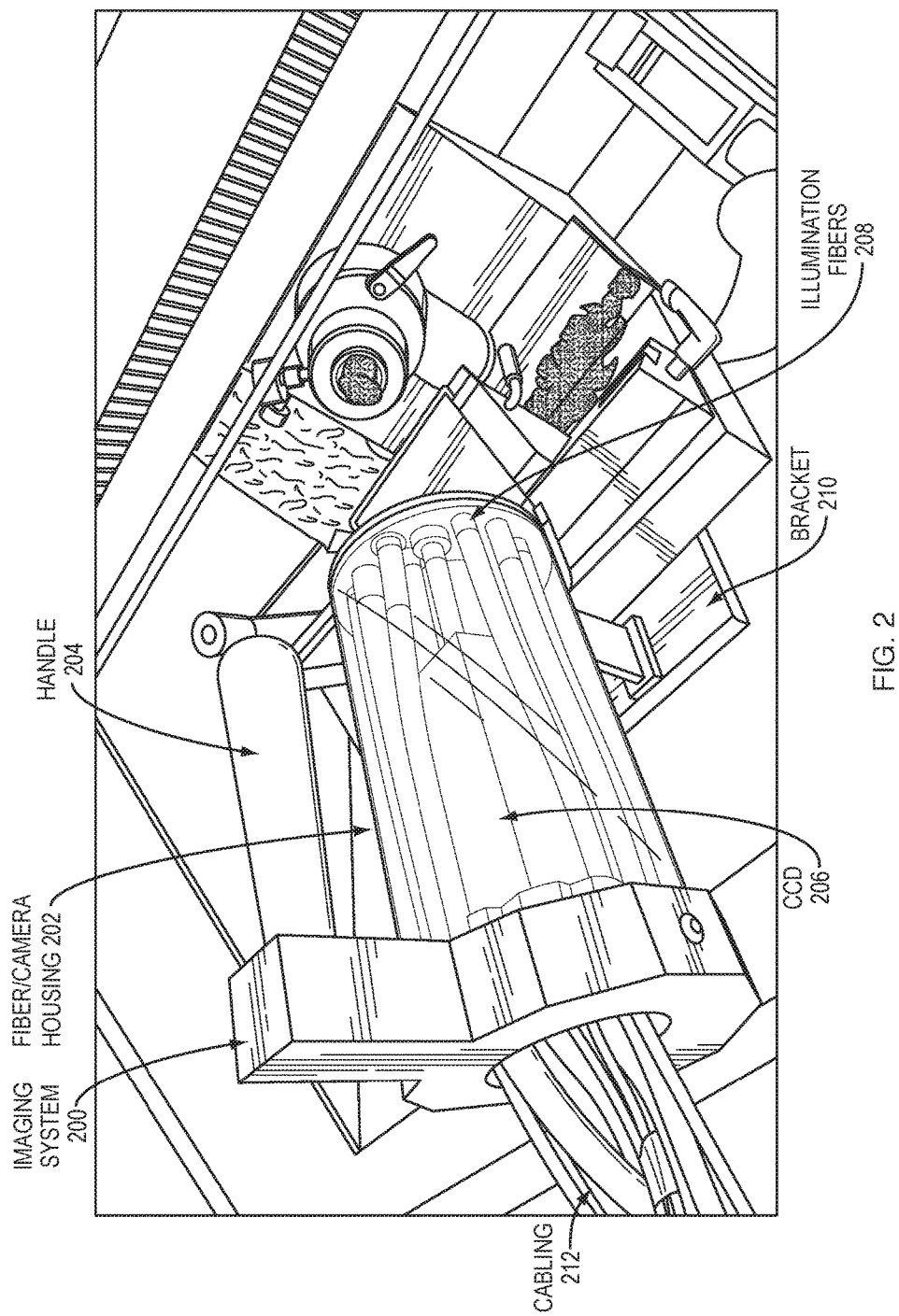
FIGS. 2-4 illustrate an example fluorescence histo-tomography (FHT) imaging device for use in a microtome or cryomicrotome, according to various embodiments.
Figure 3:
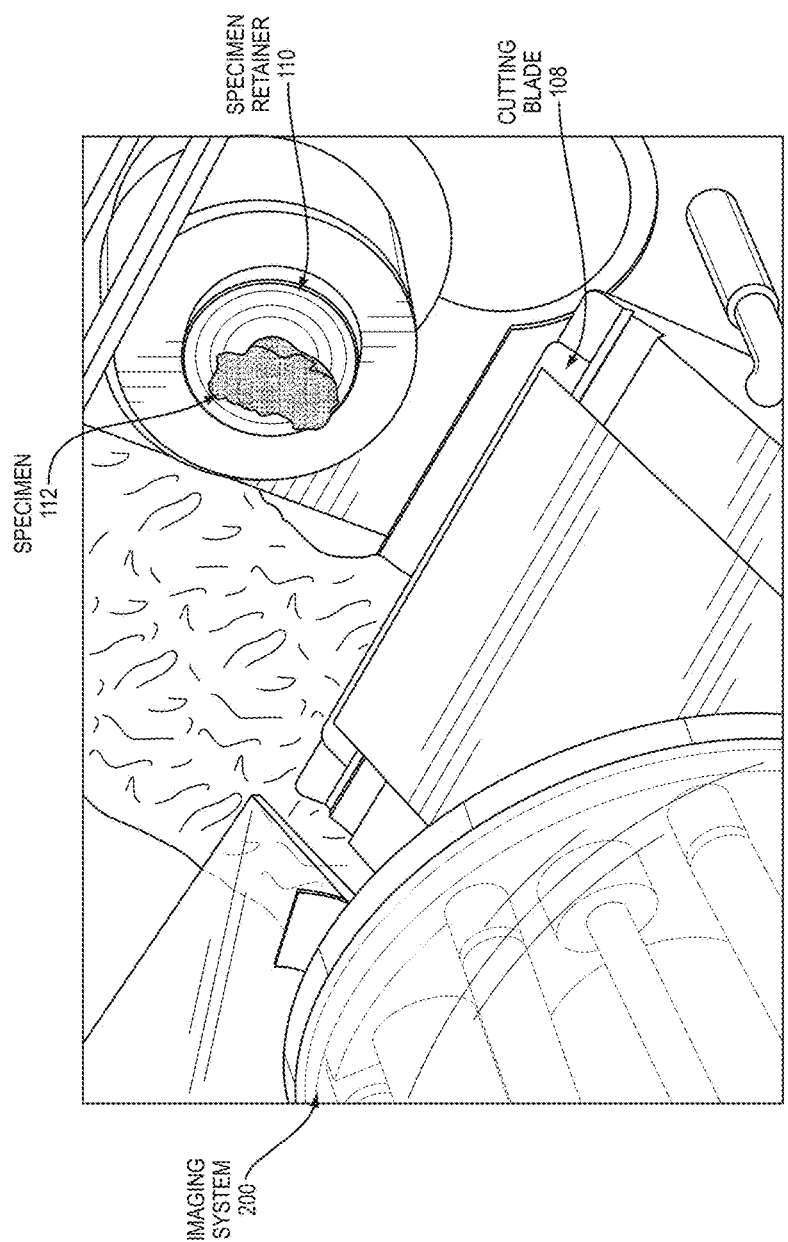
Figure 4:
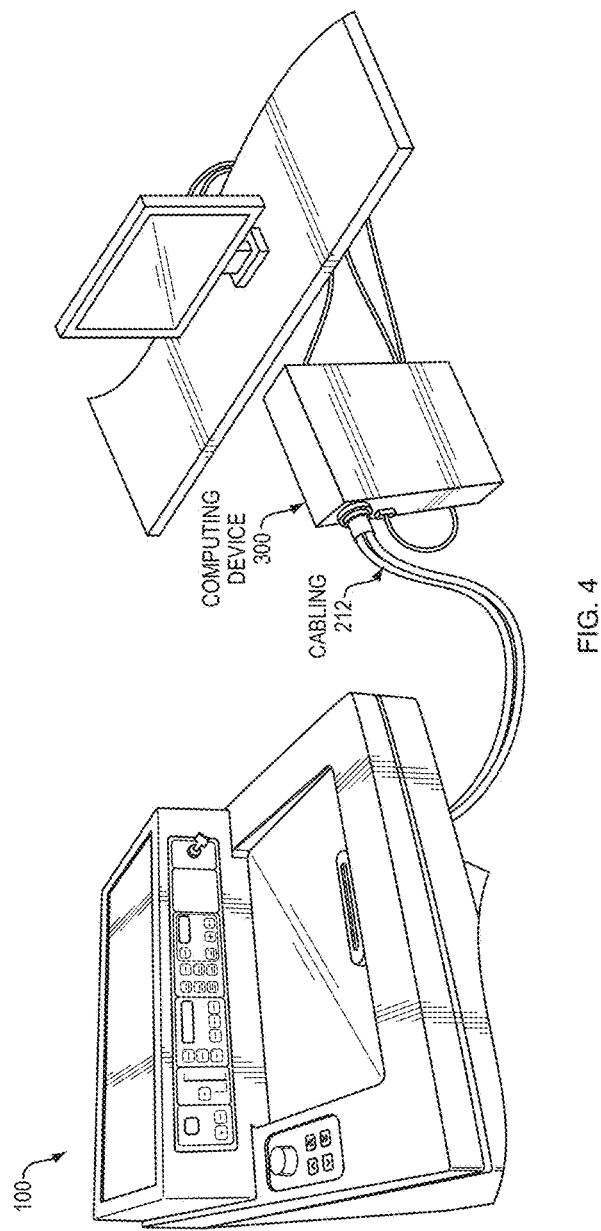

Referring now to FIGS. 2-4, a fluorescence histo-tomography (FHT) system is shown, in various embodiments. As shown in FIG. 2, the FHT system may include an imaging device/system 200 that is operable to image the exposed block face of tissue specimen 112 within chamber 106 of cryomicrotome 100. As would be appreciated, imaging system 200 may be transportable, allowing imaging system 200 to be used with any number of different types of cryomicrotomes. Advantageously, this allows a user to adapt a cryomicrotome to perform FHT imaging without having to make significant modifications to the cryomicrotome.

Imaging system 200 may include a housing 202 that houses the various imaging components of system 200. In some embodiments, housing 202 may include a handle 204 that allows the user to position housing 202 within chamber 106 of cryomicrotome 100 and/or remove imaging system 200 therefrom, as desired. Housing 202 may be formed of any suitable materials such as plastics, ceramics, or sheet metal and may protect the imaging components of imaging system 200 from the internal climate of chamber 106 of cryomicrotome 100 (e.g., to protect a camera from exposure to the colder temperatures, etc.). At least a portion of housing 202 may also be at least semi-transparent such that light in the white and NIR spectrums may pass through housing 202. Further, while housing 202 is shown with a primarily cylindrical shape, other implementations of housing 202 may take on other geometric shapes, e.g., to fit within the chambers of certain types or models of cryomicrotomes.

In various embodiments, the FHT system may also include one or more support brackets or other retaining members, to position the imaging components in housing 202 at a suitable distance within chamber 106 of cryomicrotome 100 relative to tissue specimen 112. For example, as shown, support mount/bracket 210 may contact the floor of chamber 106 and support housing 202 at a distance therefrom. While housing 202 may be positioned at any desired distance from the block face of tissue specimen 112, testing has shown that a distance of approximately ten inches yields suitable FHT imaging results of the sample while not impinging the motion of cutting blade 108, as shown in greater detail in FIG. 3.

In some embodiments, bracket 210 may be coupled or otherwise fastened to the floor of chamber 106 (e.g., via one or more screws, bolts, etc.). In other embodiments, bracket 210 may be shaped to engage one or more components of cryomicrotome 100 (e.g., to slide under the structure associated with cutting blade 108, etc.). In addition, bracket 210 may be a separate component from that of housing 202 (e.g., housing 202 rests on bracket 210), may be fastened or coupled thereto, or may be directly formed as part of housing 202, according to various embodiments.

The imaging components of imaging system 200 may include one or more cameras, such as one or more charge-coupled device (CCD) camera(s) 206 and one or more illumination light sources/fibers 208. For example, camera(s) 206 may include a white light camera configured to capture images within the visible spectrum and/or a fluorescence camera configured to capture images in the NIR or IR spectrum. Similarly, illumination light sources/fibers 208 may include one or more fibers to shine fluorescent and/or white light onto the block face of tissue specimen 112 during imaging. Extending out of the back of housing 202 may be cabling 212 that connect camera(s) 206 and illumination sources/fibers 208 to a computing device 300, as shown in FIG. 4.

In some cases, ambient illumination by room lighting may be sufficiently diffuse such that imaging system 200 does not require a dedicated white light illumination source. However, in other embodiments, imaging system 200 may further include one or more white light sources as part of imaging system 200, such as part of illumination fibers 208 or lights located on the end of housing 202, or external to housing 202 (e.g., a surgical lamp, a camera flash, etc.).

Camera(s) 206 may be of any suitable type operable to capture images in the white light and NIR spectrums. For example, one prototype of the FHT system herein uses a high resolution Canon EOS 700 white light camera available from Canon, Melville, N.Y., although any other suitable white light camera can be used in other implementations. For the fluorescence imaging, suitable systems include the K-FLARE®, and Lab-FLARE® models R1™, R1v™, RP1™, RP2™, RC2™, FLARE® (FLuorescence-Assisted Resection and Exploration) imaging systems available from Curadel LLC, Marlboro, Mass. Other suitable system components may be used, as desired, without deviating from the teachings herein.

To reduce specular reflections, imaging system 200 may include polarizers with camera(s) 206 and/or the illumination sources (e.g., illumination fibers 208). For example, imaging system 200 may use concentric linear polarizers with excitation and emission rotated at 90 degrees, which will reduce specular reflections from the illuminated tissue specimen 112.

Figure 5:
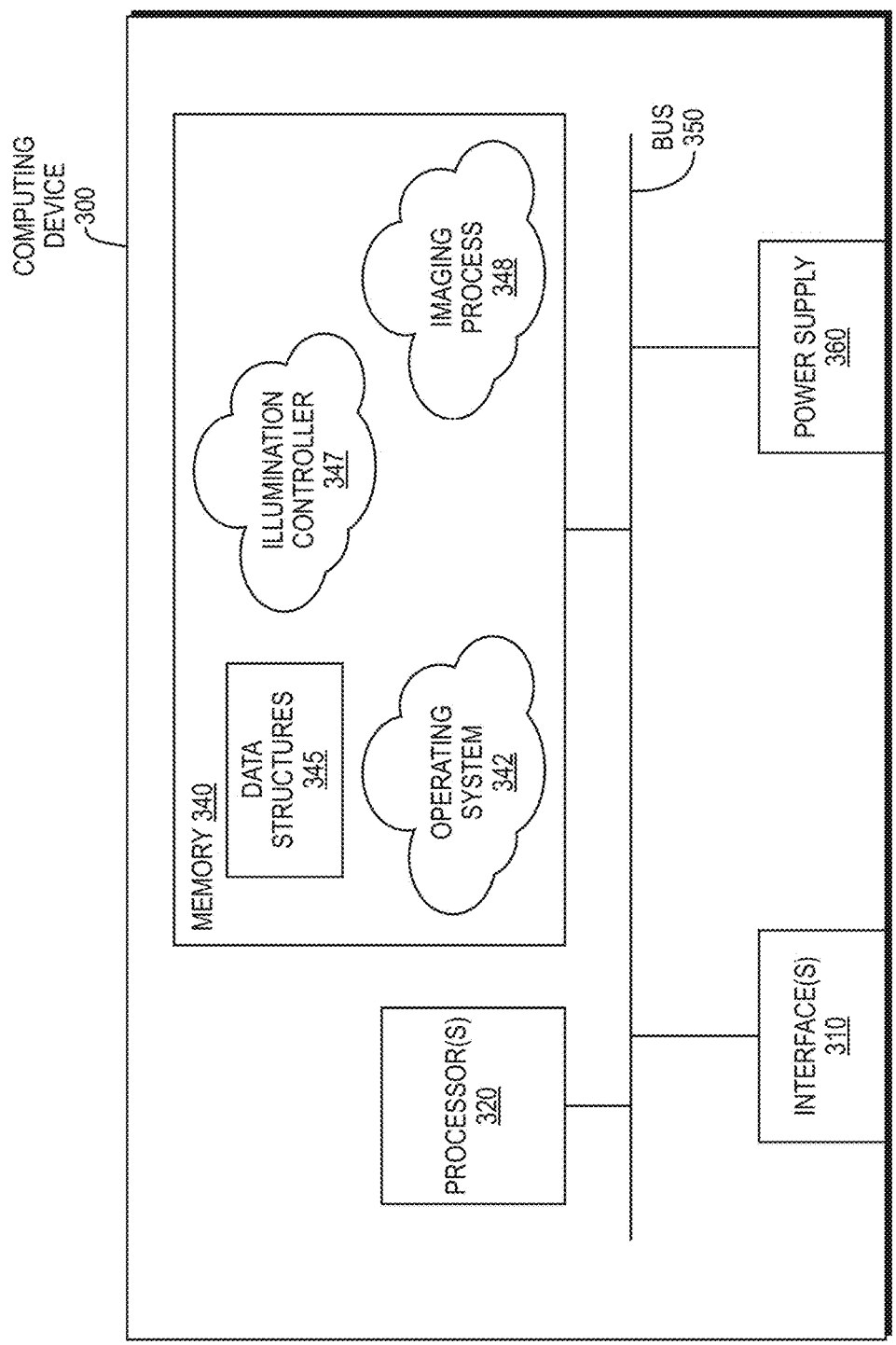
FIG. 5 illustrates an example computing device of a FHT system, according to various embodiments.

FIG. 5 illustrates an example schematic block diagram of computing device 300, according to various embodiments. As shown, computing device 300 may comprise one or more interfaces 310 (e.g., wired, wireless, etc.), at least one processor 320, and a memory 340 interconnected by a system bus 350 and powered by a power supply 360.

Interface(s) 310 contain the mechanical, electrical, and signaling circuitry for communicating data with other computing devices in the FHT system. For example, interfaces 310 may be communicatively coupled to camera(s) 206 and illumination fibers 208 of imaging system 200 via cabling 212 either directly or via any number of intermediate components. For example, interface(s) 310 may be in communication with one or more light sources for illumination fibers 208, to provide control over when the light sources are activated (e.g., to shine fluorescent light on tissue specimen 112). Further, interface(s) 310 may receive captured image data from the white light and fluorescence cameras of imaging system 200 for further image processing.

In some cases, interface(s) 310 may also be in communication with one or more user interface devices. Generally, a user interface device provides sensory information to a user and/or receives input from the user via one or more sensors. For example, user interface devices may include, but are not limited to, electronic displays (e.g., to display the resulting images of the tissue block face to the user), pointing devices (e.g., track pads, touch screens, etc.), audio equipment (e.g., speakers, microphones, etc.), and the like. Additionally, interface(s) may also communicatively couple computing device 300 to other computing devices via a hardwired or wireless network (e.g., to convey image data to another device, to receive instructions from another device, etc.).

The memory 340 comprises a plurality of storage locations that are addressable by the processor 320 and interface(s) 310 for storing software programs and data structures associated with the embodiments described herein. The processor 320 may comprise hardware elements or hardware logic adapted to execute the software programs and manipulate the data structures 345, which may include received sensor data (e.g., captured image data, etc.), operating parameters or settings, and the like. An operating system 342, portions of which are typically resident in memory 340 and executed by processor 320, functionally organizes device 300 by, inter alia, invoking operations in support of software processes and/or services executing on device 300. These software processes and/or services may comprise, in various embodiments, an illumination controller process 347 and/or an imaging process 248, as described herein.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, while the processes have been shown separately, those skilled in the art will appreciate that processes may be routines or modules within other processes.

In general, illumination controller 347 may be configured to control when the fluorescent light source, and possibly the white light source, is activated. As would be appreciated, the light source itself, such as a light emitting diode (LED), laser, etc., may be in communication with computing device 300 and may be optically coupled to illumination fibers 208, to emit the corresponding light onto the block face of tissue specimen 112. For example, illumination controller 347 may control when imaging system 200 illuminates tissue specimen 112 with NIR or IR wavelengths, to provoke an excitation response from the fluorophore(s) present within the tissue.

Imaging process 248 may be operable to acquire and/or process images captured by imaging system 200. For example, imaging process 248 may send control signals to camera(s) 206 to capture white light and/or fluorescence images of the block face of tissue specimen 112. In turn, imaging process 248 may receive the captured image data from camera(s) 206 and perform image processing, as described below, to generate a finalized image for output to an electronic display. In some embodiments, imaging process 348 may be further configured to control one or more automated functions of cryomicrotome 100, such as automated actuation of cutting blade 108, movement of specimen retainer 110, etc.

Figure 6:
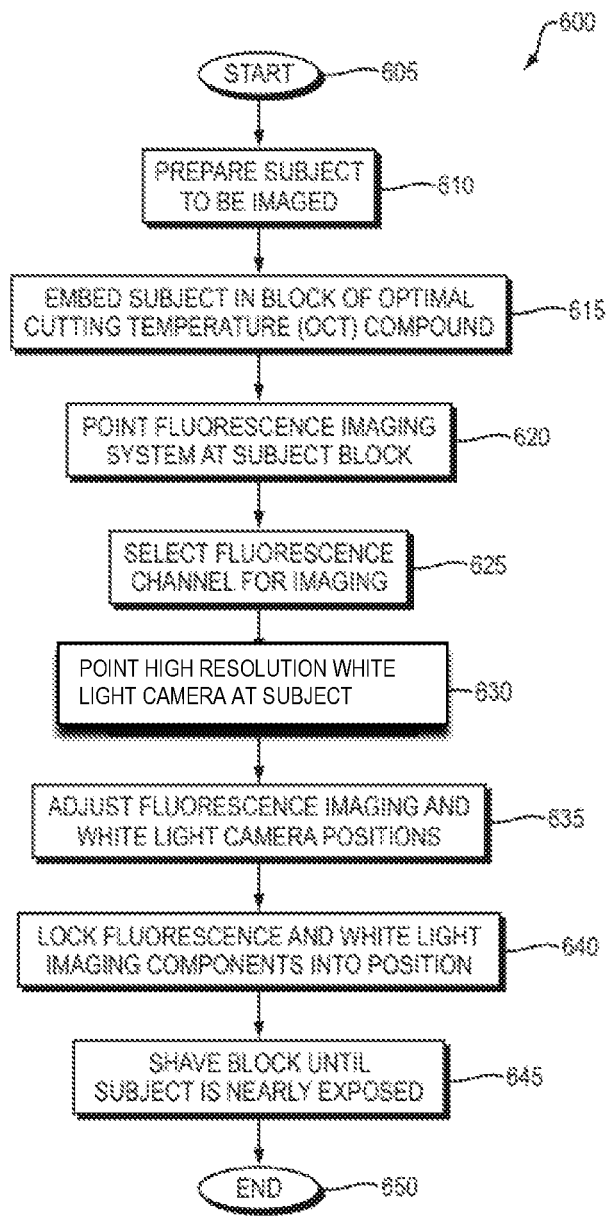
FIG. 6 illustrates an example simplified procedure for preparing a tissue specimen for FHT imaging, according to various embodiments.

Referring now to FIG. 6, an example simplified procedure 600 is shown for preparing a tissue specimen for FHT image acquisition, according to various embodiments. As shown, procedure 600 may start at step 605 and continue on to step 610 at which the subject sample/specimen is prepared. In various embodiments, this step may entail selecting a suitable fluorophore for the tissue specimen and injecting the selected fluorophore(s) into the specimen. For example, as shown previously in Table 1, different fluorophores may have different spectral properties and applications. After a suitable accumulation time subsequent to the fluorophore injection, the soft tissue for analysis may be excised.

At step 615, after preparation of the subject specimen to undergo FHT imaging, the subject may be embedded in a block of OCT compound. Any suitable OCT compound may be selected for this step. The OCT-encased subject tissue block may then be installed into position within the cryomicrotome (e.g., as shown in FIG. 1B).

Procedure 600 may also include a step 620 in which the FHT imaging system components described above are positioned and pointed at the block face of the subject block. For example, imaging system 200 may be positioned in front of the specimen block face of tissue specimen 112 within chamber 106 of cryomicrotome 100 for imaging of the block face, as described above. Notably, the fluorescence components may be positioned such that as much of the subject specimen as possible is in focus for the camera and the subject subtends the largest possible field of view without occlusion.

Procedure 600 may also include a step 625 at which a fluorescence channel is selected for the imaging system. Notably, different NIR channels may be selected, based on the fluorophore used on the tissue specimen in step 610. If multiple fluorophores are used on the specimen, the corresponding NIR channels may be selected to overlap the spectral properties of the fluorophores.

Similar to step 620, procedure 600 may include a step 630 at which a high resolution white light camera is pointed at the tissue specimen. If, for example, the white light camera and fluorescence camera are both located within the same housing (e.g., housing 202), steps 620 and 630 may be performed at the same time by positioning the housing within the chamber of the cryomicrotome relative to the tissue specimen.

At step 635 of procedure 600, the user may adjust the positions of the fluorescence and white light cameras, as needed. For example, based on test images acquired by the cameras, the positions of the cameras may be further adjusted to ensure that the desired area of the block face of the tissue is captured, the cameras are in focus, or for any other reason.

In step 640 of procedure 600, once the white light and fluorescence imaging systems are positioned at a desirable location relative to the block face of the OCT block, the components may be locked into position. For example, if the imaging components are housed within a single housing, the position of the housing within the chamber of the cryomicrotome may be solidified, once the desired position is achieved.

At step 645 of procedure 600, after preparing and mounting the tissue specimen/sample, the blade(s) of the cryomicrotome may be actuated to shave the OCT block until the tissue is nearly exposed. In other words, on completion of step 645, the exposed block face may comprise only a very fine layer of OCT compound in front of the encased tissue for imaging. Procedure 600 then ends at step 650.

Figure 7:
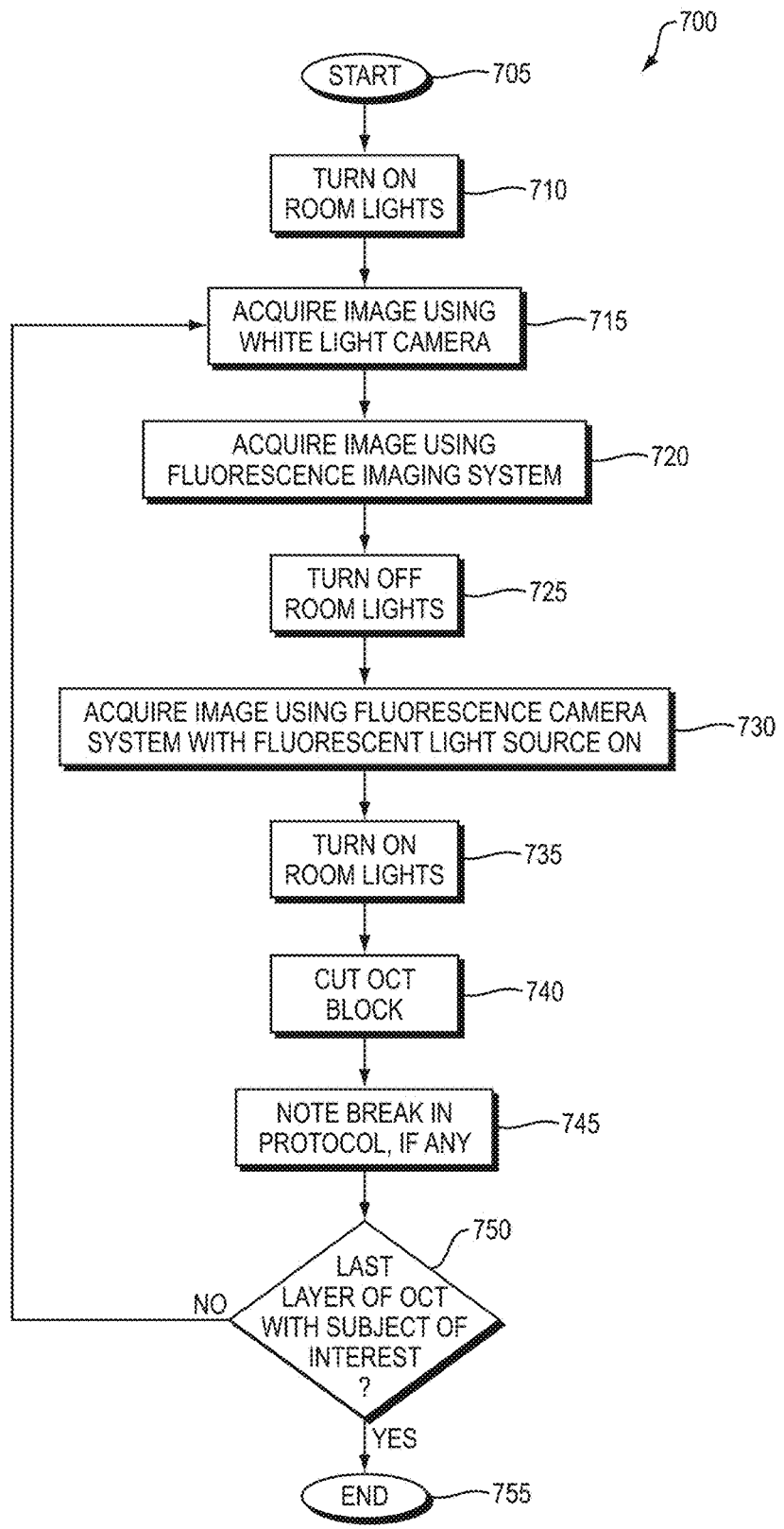
FIG. 7 illustrates an example simplified procedure for imaging a block face of a tissue specimen using FHT imaging, according to various embodiments.

Referring now to FIG. 7, an example simplified procedure 700 for performing FHT on a tissue specimen is shown, according to various embodiments. In some embodiments, procedure 700 may be performed in whole, or in part, by operating a FHT system having a computing device (e.g., device 300) in communication with an imaging system (e.g., imaging system 200). Procedure 700 may start at step 705 and continue on to step 710 where, as described in greater detail above, the room lights may be activated in the room in which the FHT system is located. Depending on the capabilities of the imaging system, ambient light from the room lights may provide sufficient white light for purposes of imaging.

At step 715 of procedure 700, the FHT system may acquire an image of the block face of the tissue specimen using its white light camera. In particular, the computing device of the FHT system may signal the white light camera to capture a high definition, white light image of the block face of the tissue specimen within the chamber of the cryomicrotome.

At step 720 of procedure 700, the FHT system may also capture one or more images using its fluorescence imaging components simultaneously with the step 715 or within a short time before or thereafter. In some embodiments, the fluorescence imaging components may capture both white light and fluorescence/NIR images of the block face of the tissue specimen. For example, the fluorescence camera may capture images of the block face with the room lights activated, with and without fluorescence illumination, as well.

At step 725 of procedure 700, the room lights may be disabled to remove the white light source from the tissue specimen. Alternatively, if a dedicated white light source is used, steps 710 and 725 may entail turning the white light source on and off, as needed.

At step 730 of procedure 700, the FHT system may also capture an image of the block face under fluorescence illumination with the room lights deactivated. Thus, as a result of steps 715, 720, and 730, the FHT system may have any or all of the following distinct images of the block face: 1.) a white light image captured by the white light camera while the block face was illuminated with white light (e.g., with the room lights on), 2.) a fluorescence image captured by the fluorescence imaging system while the block face was illuminated solely with white light, 3.) a fluorescence image captured by the fluorescence imaging system while the room lights and fluorescent light sources were both on, 4.) a fluorescence image captured by the fluorescence imaging system while all light sources were off, and 5.) a fluorescence image captured by the fluorescence imaging system while the white light source was off and the fluorescent lighting source was turned on.

At step 735, the room lights may be reactivated, after completing the imaging of the block face. In turn, at step 740, the blade(s) of the cryomicrotome may be activated to cut the OCT block, thereby exposing another portion of the sample for imaging. At or around this time, any breaks in the protocol defined by the steps above may be noted at a step 745. For example, if a superfluous image was taken, a note may be may and associated with any of the images captured of the exposed block face, thereby allowing these images to be discarded or otherwise ignored.

At step 750 of procedure 700, a decision may be made as to whether the removed layer of tissue from the OCT block is the last layer of interest. If not, procedure 700 may return to step 715, thereby repeating steps 715-745 for the newly exposed layer. However, if the final layer of tissue has been imaged, procedure 700 may continue on to step 755 where procedure 700 then ends.

It should be noted that while certain steps within procedures 600-700 may be optional as described above, the steps shown in FIGS. 6-7 are merely examples for illustration, and certain other steps may be included or excluded as desired. Further, while a particular order of the steps is shown, this ordering is merely illustrative, and any suitable arrangement of the steps may be utilized without departing from the scope of the embodiments herein. Moreover, while procedures 600-700 are described separately, certain steps from each procedure may be incorporated into each other procedure, and the procedures are not meant to be mutually exclusive.

Figure 8:
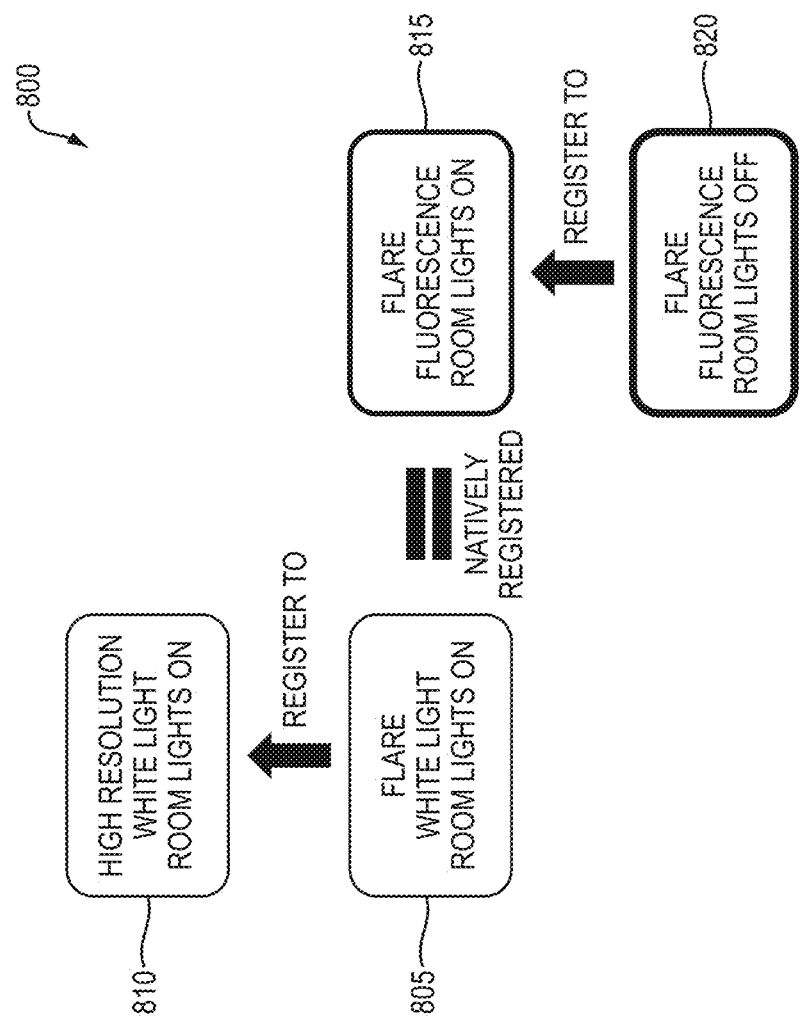
FIG. 8 illustrates an example registration scheme for images captured by a FHT system, according to various embodiments.

Referring now to FIG. 8, an illustration 800 is shown of the registration of images within a FHT system, according to various embodiments. In particular, the FHT computing device (e.g., device 300 executing imaging process 248) may co-register the various captured images (e.g., images captured via procedure 700 shown in FIG. 7), to generate the finalized image(s). The finalized images may then be provided to an electronic display or another user interface device, for review by a human user.

For purposes of illustration, assume the following labels are assigned to their corresponding images:

WL_FLARE_ON: the image 805 captured in the white light channel of the fluorescence imaging system of the block face illuminated with white light.

WL_FLARE_OFF: the image captured in the white light channel of the fluorescence imaging system of the block face with all white lights off but fluorescence excitation light on.

FL_FLARE_ON: the image 815 captured in the fluorescence channel of the fluorescence imaging system with the block face illuminated with both fluorescence excitation and white light.

FL_FLARE_OFF: the image 820 captured in the fluorescence channel of the fluorescence imaging system with the block face illuminated solely with fluorescent excitation light.

WL_HIGH_ON: the image(s) 810 captured by the high resolution white light camera with the block face illuminated with white light.

In various embodiments, the computing device may perform image processing by performing any or all of the following, as shown in FIG. 8:

1. Co-register WL_HIGH_ON images to themselves, creating an aligned image stack.
2. Co-register WL_FLARE_ON to WL_HIGH_ON.
   a. FL_FLARE_ON is natively co-registered to WL_FLARE_ON.
3. Co-register WL_FLARE_OFF to FL_FLARE_OFF.
4. Perform next-image fluorescence processing on the aligned FL_FLARE_OFF.

Notably, the computing device may perform co-registration on a per-image basis, with the exception of the WL_HIGH_ON images.

As would be appreciated, the above procedures are exemplary only and are not intended to limit the teachings herein. Notably, the above procedures may be of particular use in cases where the output of the fluorescent light source is comparable to the white light source (e.g., stray room lighting, etc.). However, if the fluorescent light signal is sufficiently high, the above techniques may be modified to allow for single-slice white light and fluorescence images to be captured simultaneously with the room lights on and natively co-registered to each other. In particular, optical filters may be used on the fluorescence image in such cases, thereby simplifying the image captures under different lighting conditions. In some embodiments, the imaging components may instead comprise the LAB-FLARE® imaging system from Curadel, LLC or a similar system. Such systems may allow for the simultaneous acquisition of different images (e.g., color and NIR, etc.), thereby eliminating the need to switch off and on the white light source (e.g., the room lights).

Example—Twine Imaging

FIGS. 9A-9I illustrate test results of FHT imaging of a fluorophore-infused piece of twine, according to various embodiments. In particular, imaging of a piece of twine comprising a plurality of individual strands was performed as a proof-of-concept using a prototype FHT system employing the techniques herein. During testing, the following steps were performed:

Kitchen twine was soaked in fluorophore (AlexaFluor 647, 100 nM concentration) for 10 minutes.
The twine was dried and wrapped around a OCT pillow.
The wrapped pillow was embedded in a larger OCT block and frozen for slicing by the FHT system.
Image data was acquired at 50 um thick sections through the OCT block.
The camera sub-system was positioned approximately 15 cm above the block, resulting in a field of view (FOV) of ~5×5 cm and a transverse pixel size of ~0.085 mm.

Figure 9A:
Figure 9B:
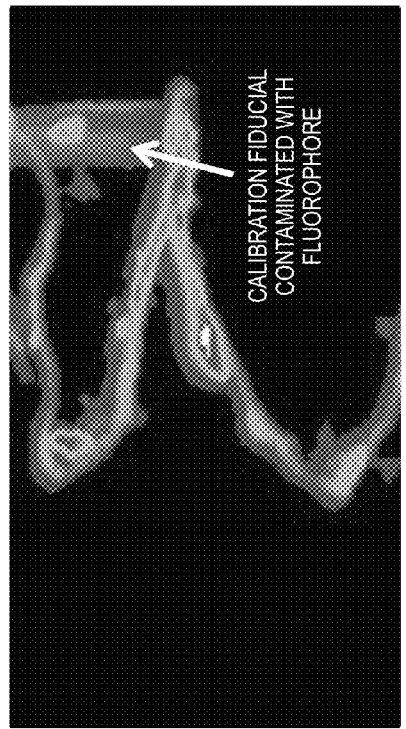

FIGS. 9A-9B illustrate the original captured images 900-910 of the twine using the FHT system. As shown, images 900-910 demonstrate a contrast between the portions of the twine that have high concentrations of the fluorophore and the portions of the twine that do not.

Figure 9C:
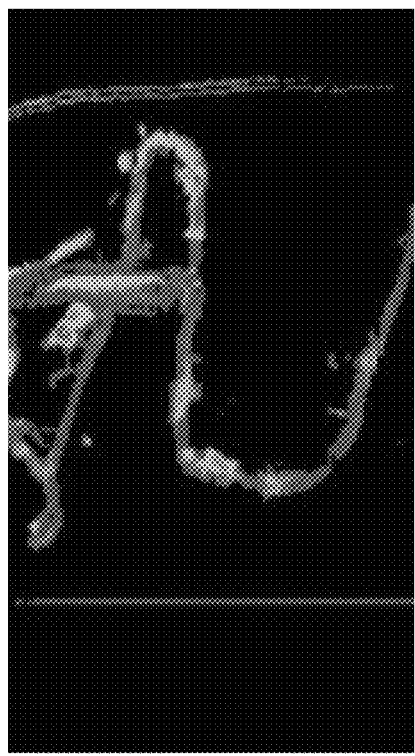
Figure 9D:
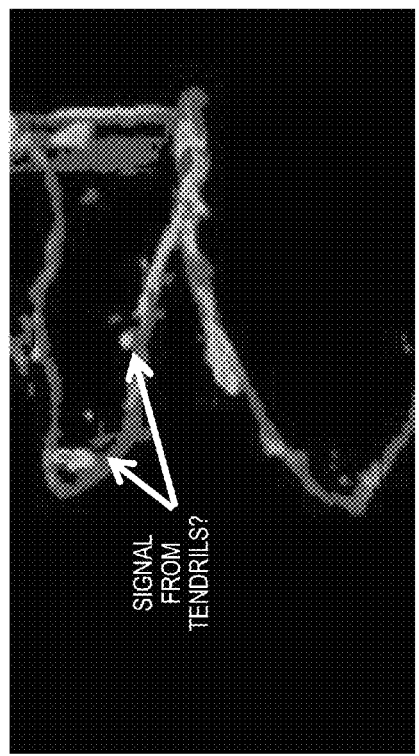

According to various embodiments, the FHT system may further employ subtraction-based deblurring, to produce an image for display. FIGS. 9C-9D illustrate images 900-910, respectively, after performing subtraction-based deblurring. According to some embodiments, the deblurring may also involve running a Monte Carlo simulation, using a point spread function method, or performing a deconvolution method. The deconvolution method may include one of a measured point spread function kernel, a simulated point spread function kernel, a Richardson-Lucy method, a Weiner filter deconvolution, a Van Cittert deconvolution, a blind deconvolution, or a regularized deconvolution method.

FIGS. 9E-9F illustrate further images 930-940 of the twine in both original and deblurred forms, respectively.

FIGS. 9G-9I also depict images 950-970 of area 942 of image 940, to illustrate the application of different image processing techniques to the images. In particular, image 950 illustrates area 942 in its original form from the fluorescence imaging system. Image 960 in FIG. 9H then illustrates image 950 after performing subtraction-based deblurring. Finally, in some embodiments, the FHT system may further apply edge-preserving smoothing to image 960, resulting in image 970 shown in FIG. 9I.

Example—Brain Tissue Imaging

Ex vivo imaging methodologies such as immunohistochemistry, fluorescence imaging, and autoradiography have been used to study anatomy, physiology and drug or tracer distribution in either whole bodies or excised organs. These methodologies can follow and accompany in vivo imaging studies or serve as stand-alone studies themselves. Because ex vivo processing is relatively expensive and time consuming, often sections and/or images are taken at large intervals (0.1-1 mm) throughout the entire specimen. Information is lost in these gaps where sections are not collected or imaged. Further, if a three dimensional model of the specimen is required, interpolation of largely spaced sections is required and the model may suffer.

To address some of these potential drawbacks, as described above, high resolution white light and multispectral (700 and 800 nm) fluorescence images may be captured off the block after every pass of the micro- or macrotome blade using an intraoperative fluorescence imaging system, thus vastly improving the amount of information captured throughout the specimen and decreasing total acquisition time. Generally, the process of fluorescent and high resolution white light data collection and subsequent co-registration and/or three-dimensional reconstruction, is referred to herein as cryofluorescence tomography or FHT.

Using the FHT techniques herein, organs or small animal whole bodies may be sectioned (e.g., at 25 microns, etc.) and all images may be captured and acquired in less than 2 hours, improving some shortcomings of various ex vivo techniques, while enabling the creation of high resolution 3D models.

To investigate the ability of FHT to study the physiology of the brain, XenoLight RediJect 2-Deoxy-D-glucose (2-DG, PerkinElmer, 750 nm excitation), a fluorescent glucose metabolism tracer, was injected into the intrathecal space of a rat. After 1.5 hours of distribution, the animal was sacrificed, the brain tissue excised, and the sample was cryopresevered in OCT. With each pass of the microtome blade (25 micron spacing), a high resolution white light and fluorescent image was acquired.

Further, to study the anatomy of ventricles and subarachnoid space, a fluorescent zwitterionic compound ZW800-1 (Curadel, LLC) was injected into the rat intrathecal space. This compound is not expected to cross into the brain parenchyma due to its chemical properties. As shown, ZW800-1 signal is constrained in the ventricles and subarachnoid space, while it is noticeably absent in brain parenchyma. One can begin to build a high resolution, three-dimensional map of the ventricles and subarachnoid space.

Figure 10A:
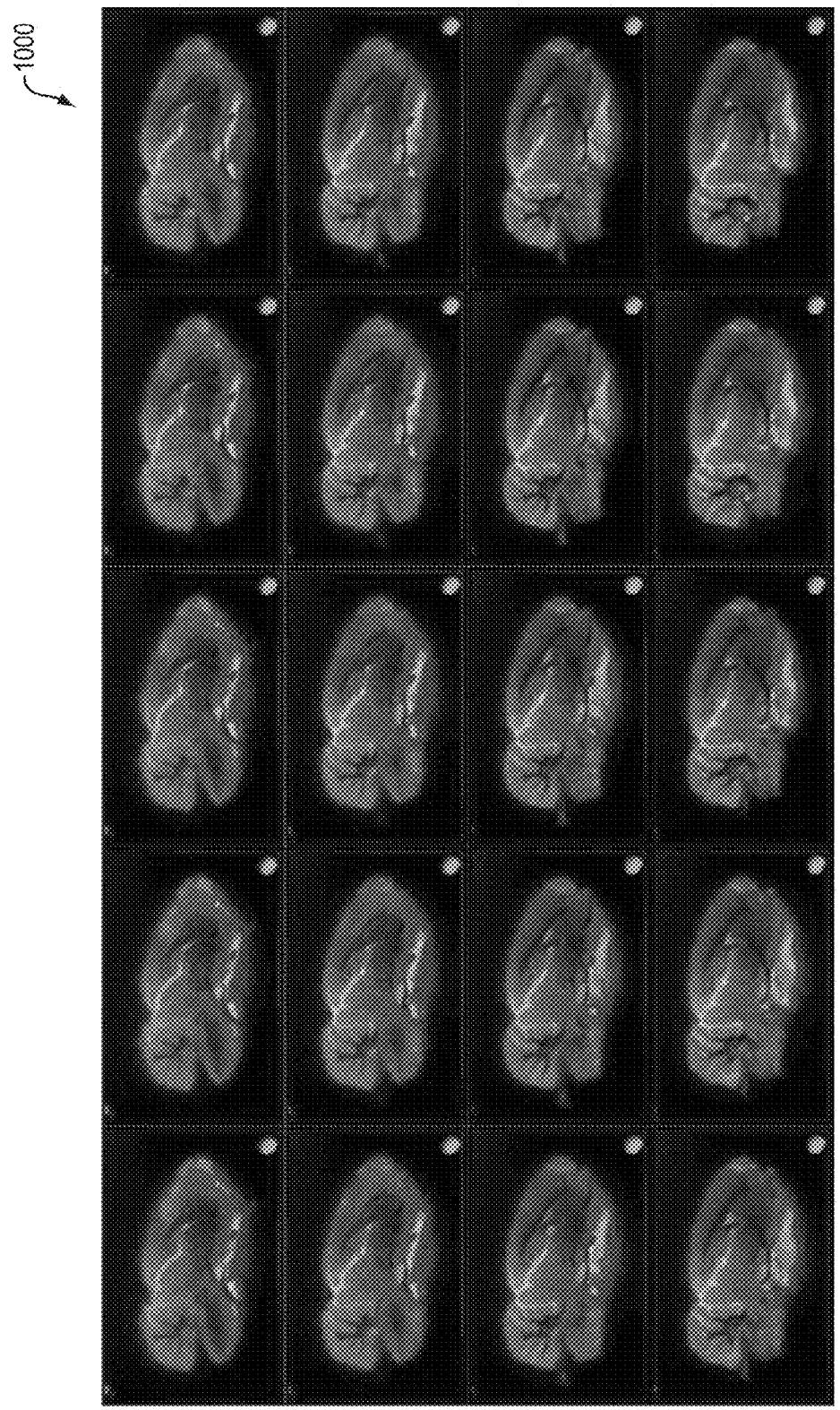
FIGS. 10A-10B illustrate test results of FHT imaging of brain tissue, according to various embodiments.
Figure 10B:
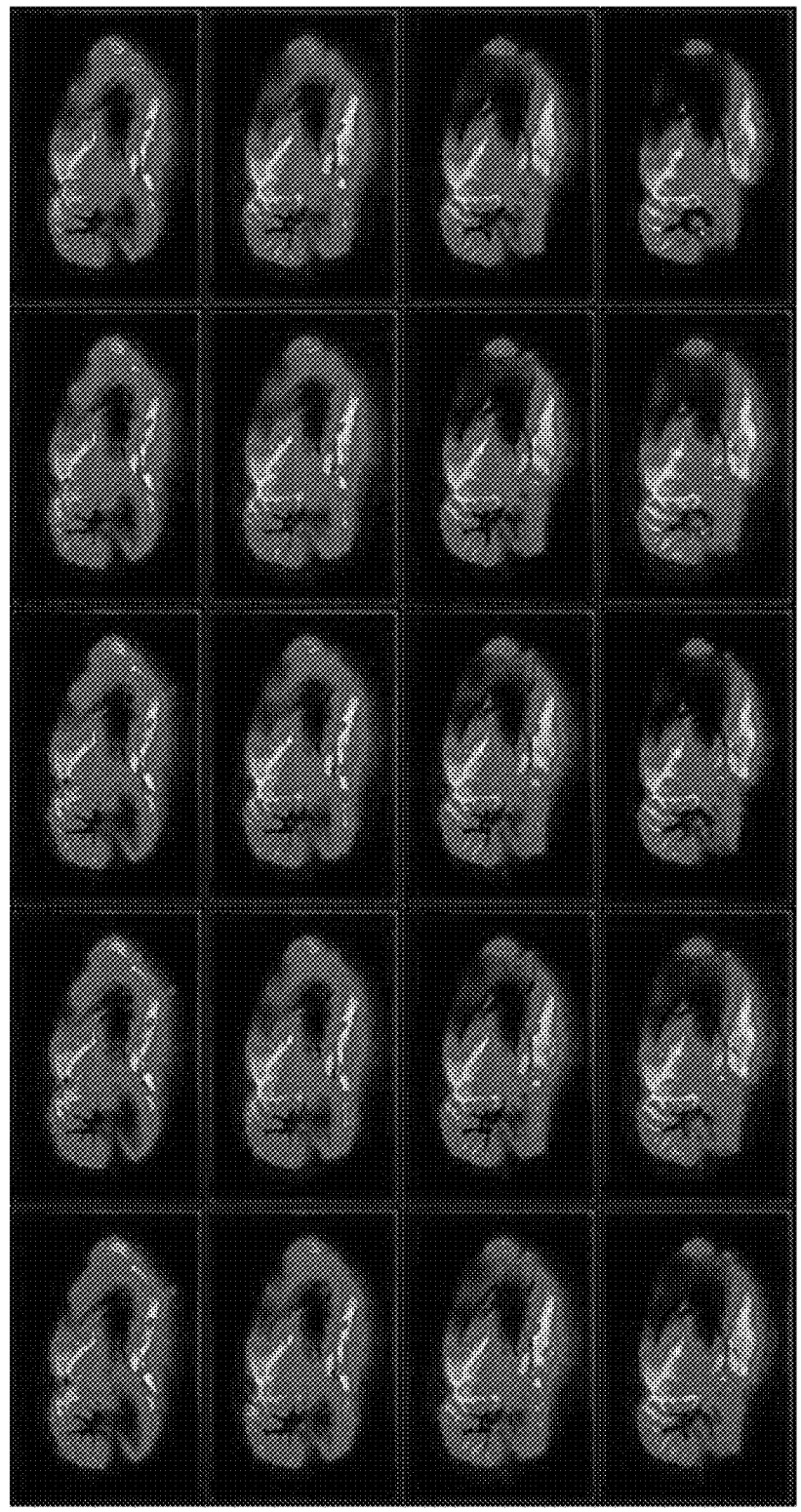
Figure 11A:
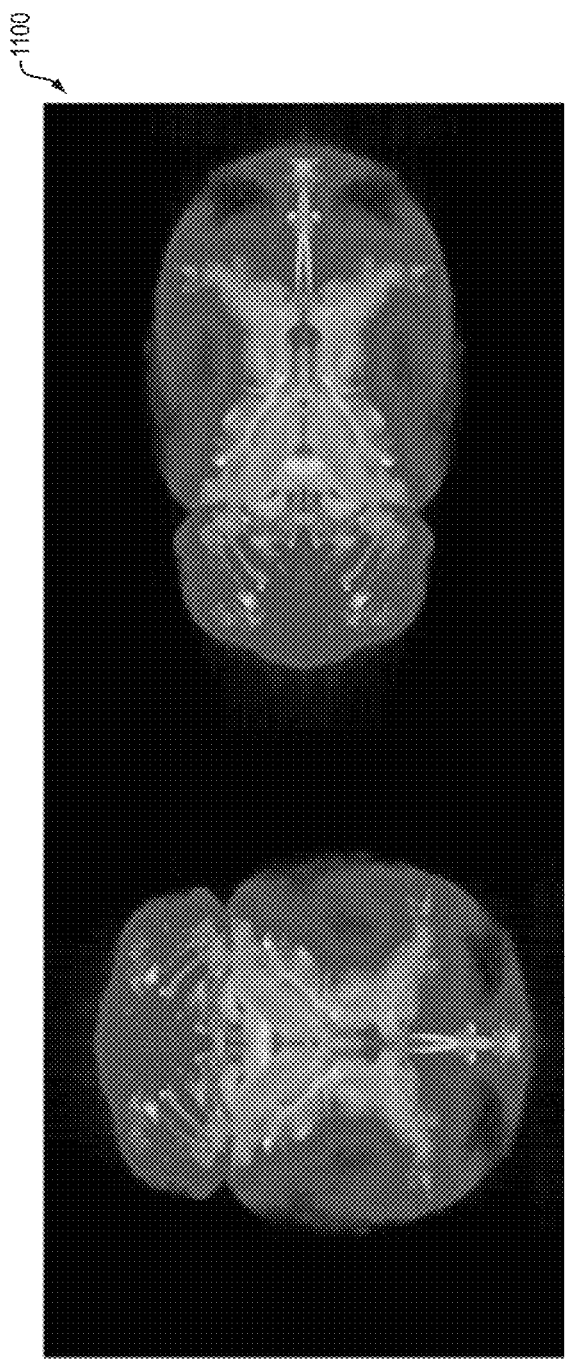
FIGS. 11A-11F illustrate further test results of FHT imaging of brain tissue, according to various embodiments.
Figure 11B:
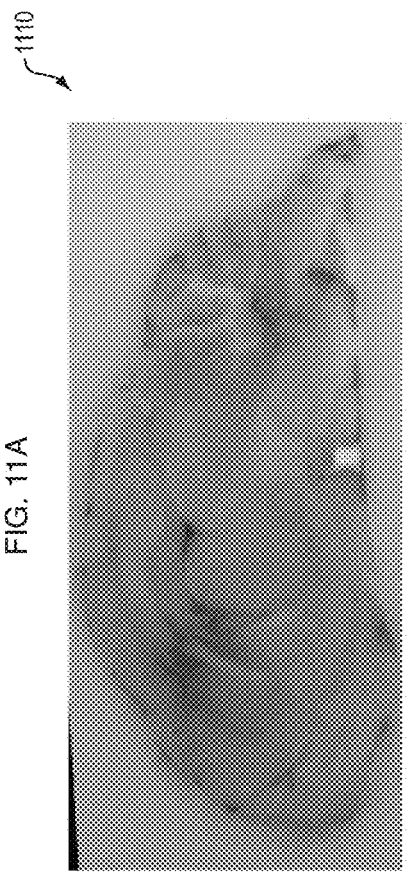
Figure 11C:
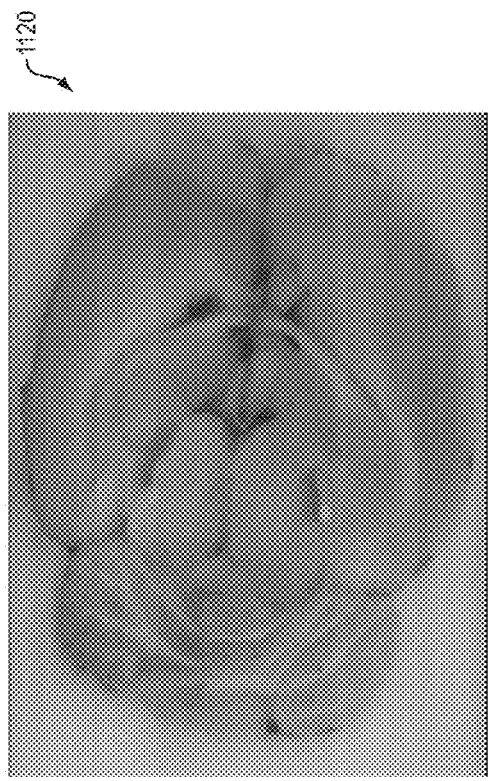
Figure 11D:
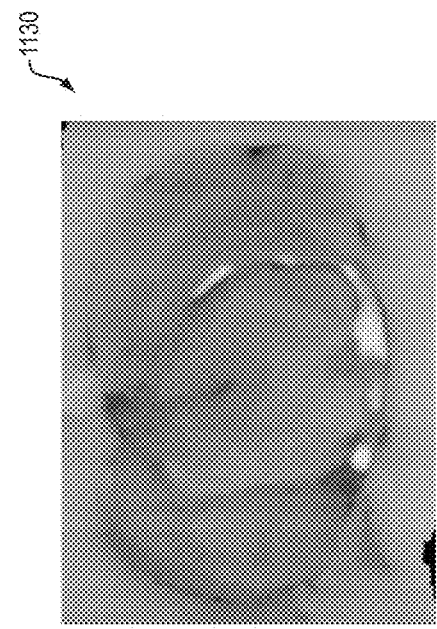
Figure 11E:
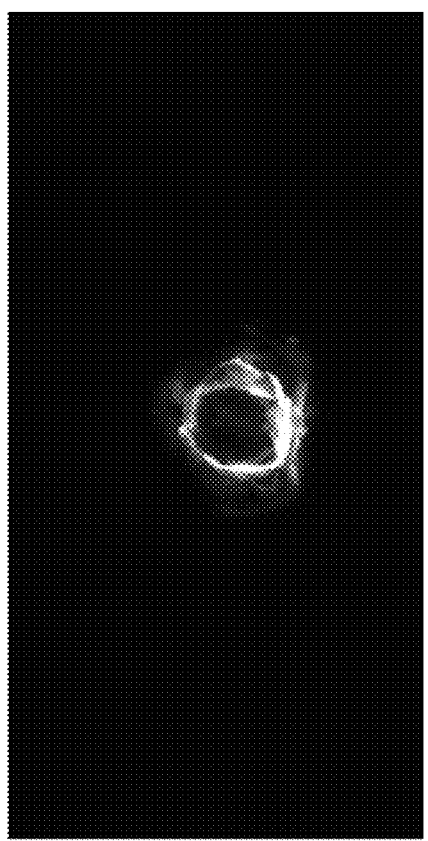
Figure 11F:
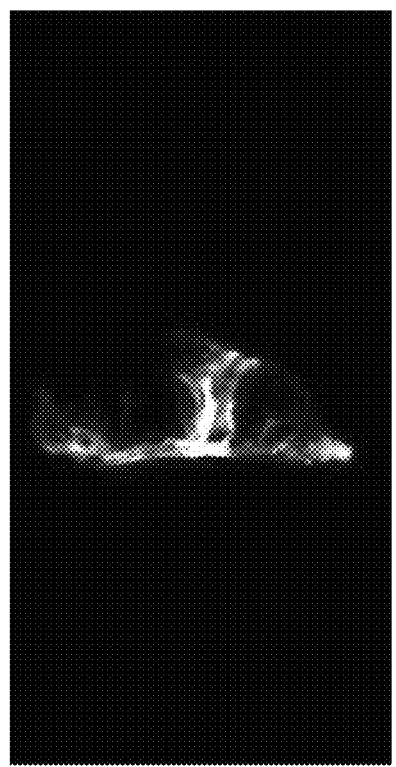

Various images captured during testing are shown in FIGS. 10A-12I. Notably, FIG. 10A-10B depict images 1000 and 1010 of the brain tissue with the white light captures colored gray and the fluorescence images colored orange/purple. FIG. 11A illustrates FHT images 1100 using maximum intensity projection (MIP). FIGS. 11B-11D illustrate sagittal, coronal, and transverse dual camera static images 1110-1130, respectively (e.g., images 1110-1130 are combined images of the white light and fluorescence captures). FIG. 11E-11F illustrate dual camera, MIP images 1140-1150, respectively.

FIGS. 12A-12C illustrate white light images 1200-1220 of the coronal, axial, and saggital planes, respectively. FIGS. 12D-12F illustrate fluorescent images 1230-1250 of the 2-DG taken up in the brain parenchyma along the coronal, axial, and saggital planes respectively. Finally, images 1260-1280 depict the fluorophore, ZW800-1 constrained in the ventricles and subarachnoid space.

Thus, as would be appreciated, FHT serves as a multi-spectral, high resolution, and time efficient ex vivo tool to study anatomy, physiology, and drug/tracer distribution, either in concert with in vivo studies or as a stand-alone study.

Example—Pharmacokinetic and Pharmacodynamic Imaging of Intrathecally Administered Anti-Sense Oligonucleotides Antisense oligonucleotides (ASOs) are promising drugs for treating central nervous system (CNS) disorders due to their specific targeting and extended pharmacological effect. The development of therapeutics for CNS disorders has been impeded by the inability of most drug molecules to cross the blood brain barrier (BBB) and engage their targets. The intrathecal (IT) dosing route offers a solution for bypassing the BBB and delivering drugs directly to the CNS. However, determining the pharmacokinetics (PK) and pharmacodynamics (PD) presents unique challenges imposed by anatomical and functional properties of the IT space and reliance upon ex vivo histological molecular techniques.

In some aspects, imaging approaches are disclosed herein using radio and fluorophore-labeled ASOs tracking PK. Further aspects of the techniques herein employ neuroreceptor targeting ASOs to enable tracking of PD using receptor-targeting radiotracers. During testing, these PK/PD principles were evaluated using two ASOs which target the MALAT1 house keeping gene and the GABA-A receptor subunit GABRA1. Dynamic SPECT/CT imaging with the 125I-MALAT1 ASO showed widespread time and dose dependent exposure of the neuroaxis tissues following lumbar IT injections, with increased exposure in cortical structures versus basal ganglia. A dosing study using either unlabeled GABRA1 or MALAT1 ASO (n=4 per cohort) demonstrated progressive decline in 18F-flumazenil uptake specific to the GABRA1 ASO, with the effect being much greater in cortical structures as compared to basal ganglia. We confirmed that the reduction of 18F-flumazenil uptake corresponded to GABRA1 mRNA and protein reduction produced by the ASO.

According to various embodiments, a 3D-FHT imaging technique was developed to demonstrate the correlation between the distributions of the IT administered Cy7-labeled GABRA1 ASO with the regional receptor knockdown demonstrated in the 18F-flumazenil. This 3D cryofluorescence imaging technique offers a bridge between in vivo molecular imaging and ex vivo histology enabling the 3D visualization of the PK/PD relationship for ASO therapy.

Specifically, during testing, two groups of four rats were treated with a single dose of anti-sense oligonucleotide (ASO) targeting MALAT1 or GABRA A. The rats underwent 1 hour dynamic $^{18}$F-flumazenil PET scans at baseline (day prior to ASO treatment), then at 1, 2, 3, 4 weeks post treatment. Phamacodynamics of treatment is followed by $^{18}$F-flumazenil PET, pharmacokinetics and distribution demonstrated by Cy7-labeled GABRA1 ASO.

Figure 13A:
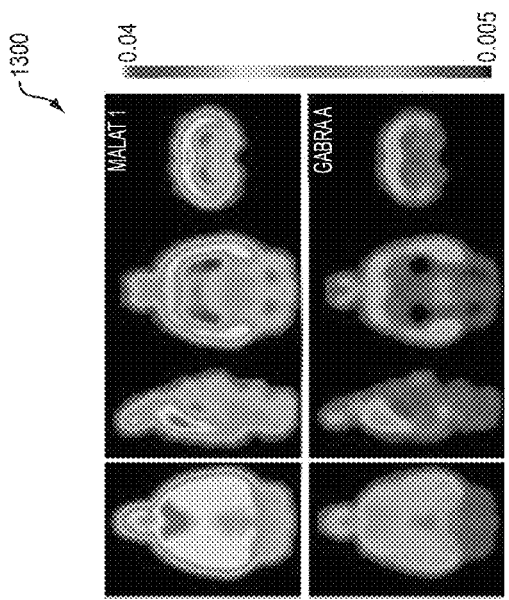
FIG. 13A-13E illustrate examples of the imaging of intrathecally-administered anti-sense oligonucleotides, according to various embodiments.

Image 1300 in FIG. 13A illustrates averaged MIP, sagittal, coronal and transverse $^{18}$F-flumazenil PET area under the curve (AUC) images for MALAT1 and GABRA A ASO-treated groups at 4 weeks post single-dose treatment. Images were co-registered to a common atlas space and scaled to units of decay-corrected uCi-min. Note the decreased $^{18}$F-flumazenil uptake post GABRA A versus MALAT1 ASO treatment.

Figure 13B:
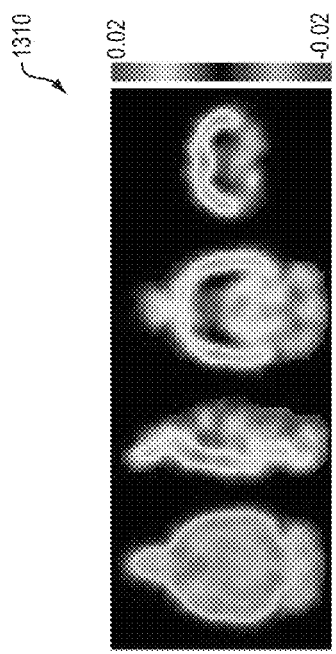

FIG. 13B shows an image 1310 illustrating the MIP, sagittal, coronal and transverse $^{18}$F-flumazenil PET (AUC) difference images between MALAT1 and GABRA A ASO treated groups at 4 weeks post single-dose treatment for N=4 rats per group. Note most voxels show positive or no change between groups.

Figure 13C:
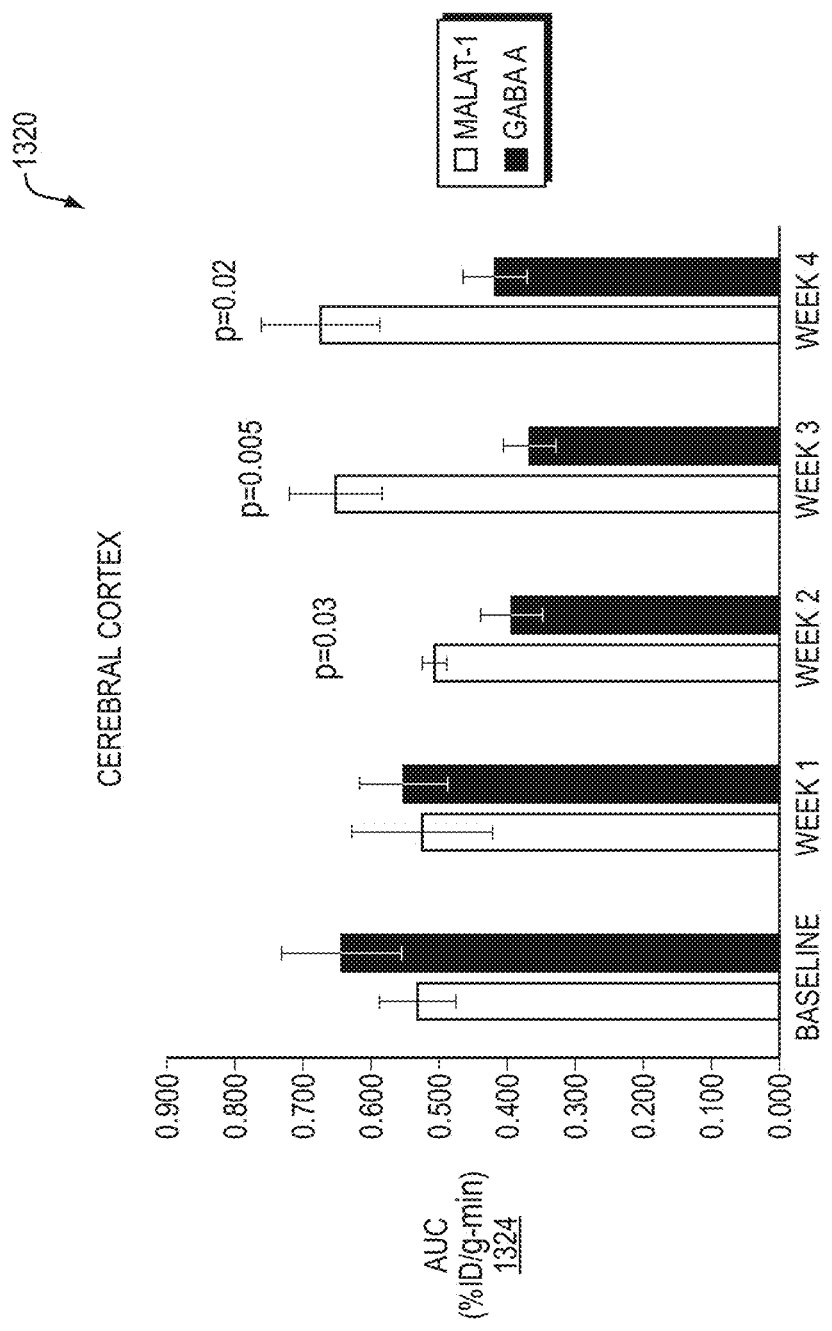

FIG. 13C illustrates a graph 1320 of the $^{18}$F-flumazenil PET (AUC axis 1324) for volume of interest on cerebral cortex at baseline and at 1, 2, 3 and 4 weeks post single dose ASO treatment (time axis 1322). The cortex uptake showed significant reduction in GABRA A versus MALAT1 targeted treatment a 2, 3, and 4 weeks.

Figure 13E:
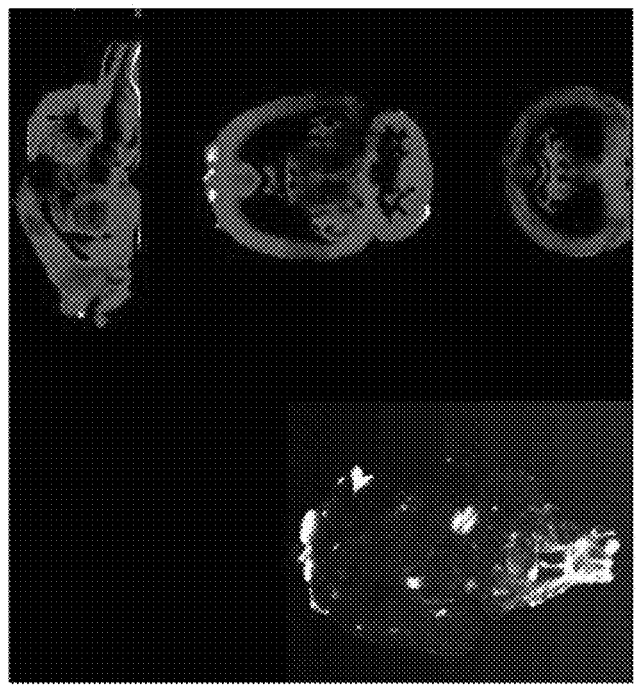
Figure 13D:
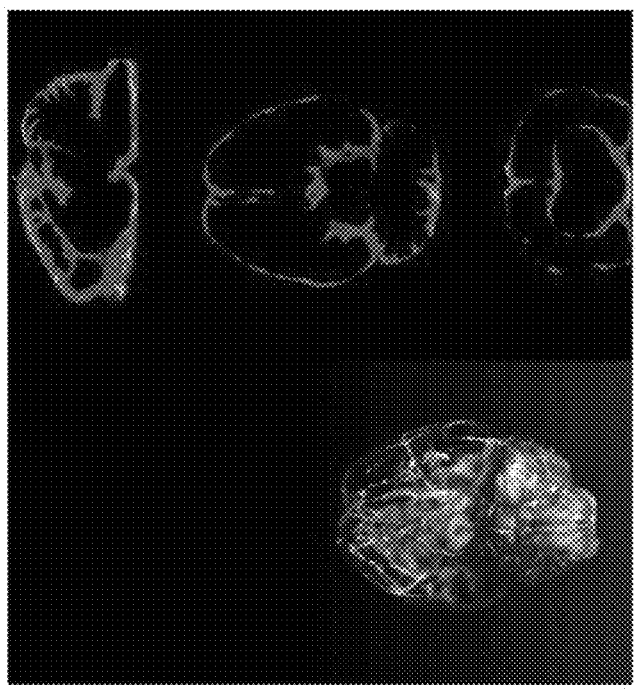

FIG. 13D depicts an image 1330 of the MIP sagittal, coronal and transverse 3D-FHT images of IT administered Cy7-labeled GABRA1 ASO at 1 hour post administration.

FIG. 13E shows an image 1340 of the MIP sagittal, coronal and transverse 3D-FHT images of IT administered Cy7-labeled GABRA1 ASO at 4 days post administration.

Clearing Tissue Slices

As noted during implementation of the techniques herein, the cut tissue slice may "stick" to the remaining tissue block after slicing, either due to electrostatic, hydrophobic, or other interactions between the slice and the block. Accordingly, in some embodiments, the FHT system may further include a mechanism that blows a puff of gas, such as air, or a non-humidity-containing gas such as nitrogen, onto the block face at the end of a slicing cycle to remove any tissue that might otherwise stick to the block and obscure imaging.

Figure 14A:
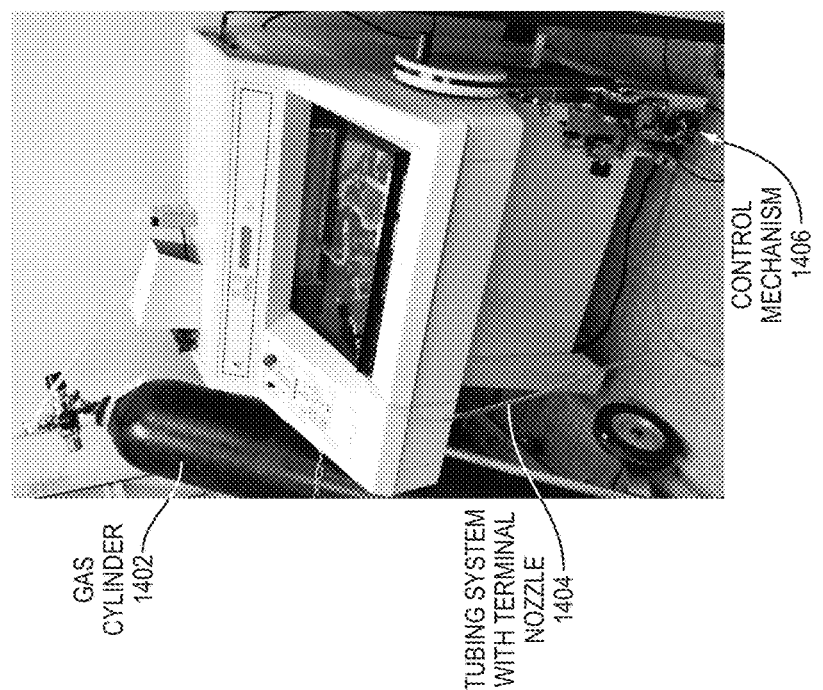
Figure 14C:
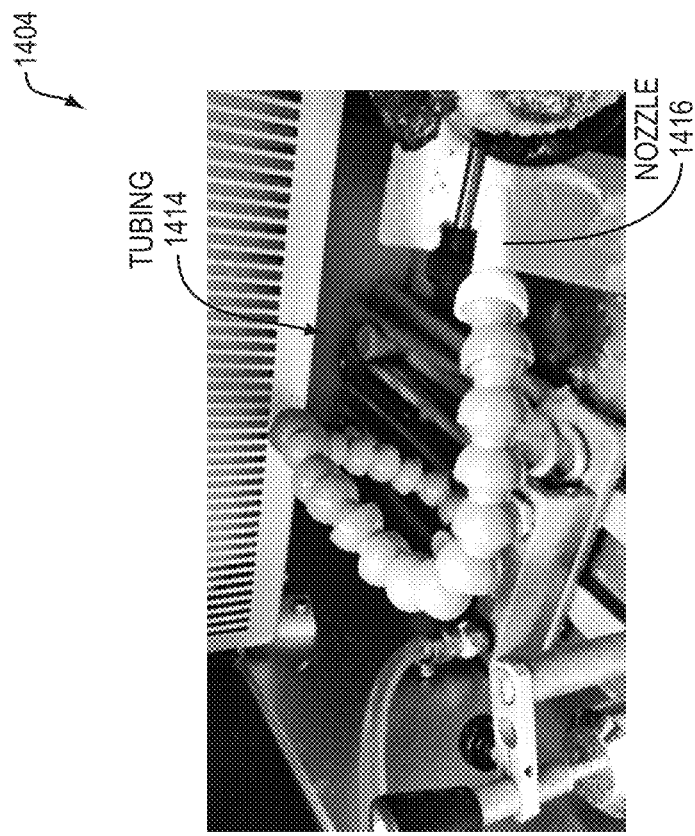

Referring now to FIGS. 14A-14C, examples are shown of a mechanism to remove stuck tissues slices from an FHT system, according to various embodiments. As shown, the mechanism may generally include a gas cylinder 1402 that stores a gas such as air, nitrogen, or argon. As would be appreciated, any form of gas may be selected as desired, depending on the type of tissue specimen, environmental conditions, etc. For example, in the case of cryo-applications (e.g., in a cryomicrotome), it is important that the gas does not have water vapor (i.e., humidity), as water vapor can freeze and block the flow the gas. Thus, for such cryo-applications, gases such as nitrogen and argon may be preferable.

Generally, gas cylinder 1402 may be pneumatically coupled to the FHT system via a tubing system 1404 and a control mechanism 1406, as shown in FIG. 14A. In particular, control mechanism 1406 may be configured to regulate the flow of gas from gas cylinder 1402 through tubing system 1404 and onto the face of the tissue block, to dislodge stuck tissue slices. In other words, control mechanism may adjust the force of the gas puff so that the gas will reliably dislodge the tissue slice completely from the block. Similarly, tubing system 1404 may convey the gas from gas cylinder 1402 onto the tissue block face via control mechanism 1406.

As shown in FIG. 14B, control mechanism 1406 may include a pressure regulator 1408, a solenoid valve 1410, and control electronics 1412, in various embodiments. Generally, pressure regulator 1408 controls the amount of gas pressure in tubing system 1404, allowing the user to adjust the pressure such that any stuck tissue slices are dislodged by the gas exiting the nozzle of tubing system 1404. Solenoid valve 1410 may also be coupled to tubing system 1404 and control the flow of gas through tubing system 1404. For example, when actuated, solenoid valve 1410 may block or unblock the flow of gas through tubing system 1404 so as to provide a puff of gas onto the block face of the tissue specimen. In some embodiments, as shown, control electronics 1412 may provide electronic or computerized control over solenoid valve 1410 and/or pressure regulator 1408, to control when the system supplies a puff of gas and/or the pressure of the supplied gas. Such electronics 1412 may either fully automate the actuation of the system or may allow a user to manually trigger the puff of gas.

FIG. 14C shows tubing system 1404 in greater detail, according to various embodiments. As shown, tubing system 1404 may include tubing 1414 that couples a nozzle 1416 to a gas cylinder 1402 via control mechanism 1406. Generally, nozzle 1416 may be located at a suitable distance from the block face of the tissue specimen and may, in some embodiments, be coupled to the slicing apparatus (e.g., a microtome, etc.), to ensure that nozzle 1416 remains pointed towards the tissue specimen after each puff of gas. For example, in the case of a cryomicrotome, tubing 1414 and nozzle 1416 may be located within the temperature-controlled chamber of the cryostat, thereby cooling the gas to the temperature of the frozen ice block. This prevents melting of the tissue block that would occur if the gas were at room temperature.

Fiducial Placement

Precise positioning of fiducial markers in a tissue block can be a difficult and time-consuming procedure. Fiducial markers are critical for FHT applications because they permit orientation of each slice relative to the original block, and permit correction for geometric and color aberrations during slicing and imaging. In some embodiments, they also permit calculation of the point-spread function, which is required to correct for the attenuation of light due to absorption and scattering, and thus reconstruction of the proper fluorescence image.

Referring now to FIGS. 15A-15B, an example apparatus 1500 for precisely placing fiducial markers in a tissue block is shown, according to various embodiments. As shown, apparatus 1500 may be configured to engage a tissue chamber 1504 in which a tissue specimen is retained. Extending through apparatus 1500 may be any number of apertures through which fiducials 1502 may be placed, thereby inserting fiducials 1502 into the tissue specimen. Apparatus 1500 may be formed of any suitable material such as ABS plastic or the like.

Preventing Damage to the Cutting Blade

Damage to the cutting blade of the histological slicing instrument may also be problematic in an FHT system, especially with automated and semi-automated systems. This occurs when the specimen retainer 110, typically made of metal, moves into the path of the cutting blade.

Figure 16:
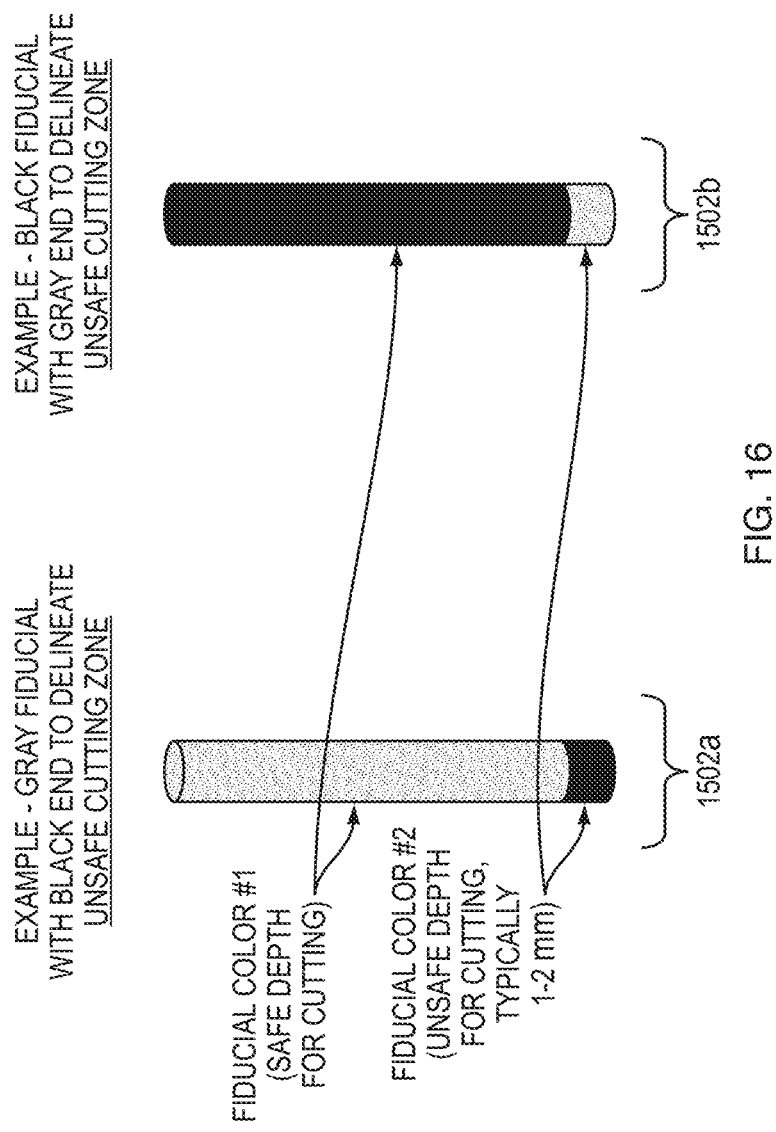
FIG. 16 illustrates an example of multi-colored fiducial markers.

Referring now to FIG. 16, an example of multi-colored fiducial markers 1502 is shown. To prevent damage to the blade of the slicing instrument, the fiducial markers 1502, such as pieces of dry Angel hair pasta, may be dipped in a solution of chemical or paint to mark one end with a color different from the original color. For example, if fiducial 1502*a* is gray in color, the distal 1-2 mm might be colored black. Or, if fiducial 1502*b* is black, such is the case with squid ink-infused pasta, the distal 1-2 mm might be painted or bleached to a gray or white color. Then, the fiducial 1502 is placed onto the specimen retainer 110 such that the end closest to the block support has the alternate color of a specified length ("the unsafe zone").

After the tissue block is placed in the slicer, and slicing begins, custom imaging software may continuously identify both the position and color of the fiducial 1502. When the color changes from the primary color to the alternate color, the software will stop all slicing, thus preventing damage to the blade. In additional embodiments, the colors throughout the vertical height of the fiducial could be selected so that the exact depth of each slice could be estimated. For example, if a 5 mm fiducial changed color every mm from red, to orange, to blue, to green, to yellow, the depth of cutting could be estimated by imaging the transition from one color to another and interpolating based on a known tissue slice depth.

The techniques herein, therefore, provide for the mounting of a FHT imaging system within the chamber of a cryomicrotome, to perform FHT imaging on the block face of a tissue specimen within the chamber. In some aspects, the imaging components of the system may be located within a transportable housing, thereby protecting the components from the conditions within the chamber and allowing a user to install, position, and remove the imaging components from the cryomicrotome as desired. Thus, the FHT system herein can be easily adapted for use with any number of existing cryomicrotomes without significant modification.

The methods according to the inventive concepts may be embodied as a non-transitory computer program product. Any combination of one or more computer readable storage device(s) or computer readable media may be utilized. The computer readable medium may be a computer readable storage medium. A computer readable storage device may be, for example, but not limited to, an electronic, magnetic, optical, electromagnetic, or semiconductor system, apparatus, or device, or any suitable combination of the foregoing. More specific examples (a non-exhaustive list) of the computer readable storage device would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage device may be any tangible device or medium that can store a program for use by or in connection with an instruction execution system, apparatus, or device. The term "computer readable storage device," or variations thereof, does not encompass a signal propagation media such as a copper cable, optical fiber or wireless transmission media.

Program code embodied on a computer readable storage device or computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to one or more processors of one or more general purpose computers, special purpose computers, or other programmable data processing apparatuses to produce a machine, such that the instructions, which execute via the one or more processors of the computers or other programmable data processing apparatuses, create means for implementing the functions/acts specified in the flowchart and/or block diagram block or blocks.

These computer program instructions may also be stored in one or more computer readable storage devices or computer readable media that can direct one or more computers, one or more other programmable data processing apparatuses, or one or more other devices to function in a particular manner, such that the instructions stored in the one or more computer readable storage devices or computer readable medium produce an article of manufacture including instructions which implement the function/act specified in the flowchart and/or block diagram block or blocks.

The computer program instructions may also be loaded onto one or more computers, one or more other programmable data processing apparatuses, or one or more other devices to cause a series of operational steps to be performed on the one or more computers, one or more other programmable data processing apparatuses, or one or more other devices to produce a computer implemented process such that the instructions which execute on the one or more computers, one or more other programmable data processing apparatuses, or one or more other devices provide processes for implementing the functions/acts specified in the flowchart and/or block diagram block or blocks.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A fluorescence histo-tomography (FHT) system comprising:
    a housing;
    a fluorescence camera located within the housing;
    a white light camera located within the housing;
    a fluorescence light source located within the housing; and
    a support mount configured to support the housing within a chamber of a slicing apparatus such that the cameras and fluorescence light source are aimed towards a block face of a tissue specimen retained within the chamber, wherein the support mount is removably positionable on a floor of the chamber.

2. The FHT system as in claim 1, further comprising:
    processing circuitry that includes a processor configured to execute a process and a memory to store the process executed by the processor, the process when executed operable to:
        control the white light camera to capture a white light image of a block face of a tissue specimen retained within the chamber;
        control the fluorescence camera to capture a fluorescence image of the block face under white light and fluorescence illumination;
        co-register the white light and fluorescence images to form a combined image; and
        provide the combined image to an electronic display.

3. The FHT system as in claim 2, wherein the process when executed is further operable to:
    control the white light and fluorescence cameras to capture the white light and fluorescence images of the block face simultaneously.

4. The FHT system as in claim 1, further comprising:
    a gas cylinder storing a pressurized gas;
    a nozzle coupled to the gas cylinder via tubing and positionable within the chamber of the slicing apparatus to direct the nozzle towards the tissue specimen; and
    a control mechanism coupled to the tubing that controls a flow of the pressurized gas towards the tissue specimen within the chamber via the nozzle.

5. The FHT system as in claim 1, further comprising:
    one or more multi-colored fiducials for insertion into the tissue specimen.

6. The FHT system as in claim 1, wherein the housing is portable and wherein the housing further comprises a handle to allow a user to removably position the housing within the chamber.

7. The FHT system as in claim 1, wherein the slicing apparatus comprises a cryomicrotome.

8. The FHT system as in claim 1, further comprising:
    a tissue chamber configured to retain the tissue specimen; and
    a fiducial positioning apparatus configured to engage the tissue chamber, wherein the fiducial positioning apparatus forms a plurality of apertures through which fiducials may be inserted into the tissue specimen retained within the tissue chamber.

9. The FHT system as in claim 1, wherein the fluorescence camera is configured to detect the presence of a fluorophore within the tissue specimen at a wavelength between a range of approximately 200 nm to 1000 nm, when the block face of the tissue specimen is illuminated with the fluorescence light source.

10. A method of performing fluorescence histo-tomography (FHT) comprising:
   capturing, by an imaging device mounted within a chamber of a slicing apparatus, a white light image of a block face of a tissue specimen retained within the chamber, wherein the imaging device is mounted within the chamber using a support mount in contact with a floor of the chamber;
   capturing, by the imaging device, a fluorescence image of the block face under white light and fluorescence illumination;
   co-registering, by the imaging device, the white light and fluorescence images to form a combined image; and
   providing, by the imaging device, the combined image to an electronic display.

11. The method as in claim 10, wherein the white light and fluorescence images are acquired simultaneously by the imaging device.

12. The method as in claim 10, wherein the white light image is capturing via a white light camera of the imaging device, and wherein the fluorescence image is capturing via a fluorescence camera of the imaging device.

13. The method as in claim 10, wherein the white light illumination comprises ambient light.

14. The method as in claim 10, further comprising:
   manually operating the slicing apparatus to expose a second block face of the tissue specimen; and
   generating, by the imaging device, a combined white light and fluorescence image of the exposed second block face.

15. The method as in claim 10, further comprising:
   capturing a high resolution image of the block face under white light; and
   registering the high resolution image to the white light image.

16. The method as in claim 10, further comprising:
   capturing, by the imaging device, a second fluorescence image of the block face under a low ambient light condition; and
   registering, by the imaging device, the second fluorescence image with the fluorescence image captured under white light and fluorescence illumination.

17. A fluorescence histo-tomography (FHT) system comprising:
   a portable housing having a handle to allow a user to removably position the housing within a chamber of a slicing apparatus;
   a fluorescence camera located within the housing;
   a white light camera located within the housing;
   a fluorescence light source located within the housing; and
   a support mount configured to support the housing within the chamber such that the cameras and fluorescence light source are aimed towards a block face of a tissue specimen retained within the chamber.

18. The FHT system as in claim 17, wherein a white light and fluorescence images are acquired simultaneously by the white light camera and fluorescence camera, respectively.

* * * * *